(12) United States Patent
Hanson et al.

(10) Patent No.: US 7,041,839 B2
(45) Date of Patent: May 9, 2006

(54) STEROIDAL ANTIESTROGENS AND ANTIANDROGENS AND USES THEREOF

(75) Inventors: Robert N. Hanson, Newtown, MA (US); Carolyn Friel, Boston, MA (US); Choon Young Lee, Boston, MA (US)

(73) Assignee: Northeastern University, Boston, MA (US)

( * ) Notice: Subject to any disclaimer, the term of this patent is extended or adjusted under 35 U.S.C. 154(b) by 7 days.

(21) Appl. No.: 10/297,310

(22) PCT Filed: Jun. 22, 2001

(86) PCT No.: PCT/US01/20142

§ 371 (c)(1),
(2), (4) Date: Dec. 4, 2002

(87) PCT Pub. No.: WO01/98322

PCT Pub. Date: Dec. 27, 2001

(65) Prior Publication Data

US 2004/0002484 A1     Jan. 1, 2004

Related U.S. Application Data

(60) Provisional application No. 60/213,282, filed on Jun. 22, 2000.

(51) Int. Cl.
| | |
|---|---|
| *C07J 1/00* | (2006.01) |
| *C07J 43/00* | (2006.01) |
| *C07J 71/00* | (2006.01) |
| *C07D 215/04* | (2006.01) |

(52) U.S. Cl. ............... 552/618; 552/629; 552/648; 552/649; 540/2; 540/52; 540/57; 540/109

(58) Field of Classification Search ............... 514/182; 552/618, 619, 622, 628, 642, 648, 629, 649, 552/109; 540/2, 52, 57

See application file for complete search history.

(56) References Cited

U.S. PATENT DOCUMENTS

| | | | | |
|---|---|---|---|---|
| 3,193,564 A | * | 7/1965 | Klimstra et al. | ............ 552/630 |
| 3,401,181 A | * | 9/1968 | Klimstra | .................... 552/618 |
| 4,705,783 A | * | 11/1987 | Crowe et al. | ............... 514/180 |
| 4,725,426 A | * | 2/1988 | Hofmeister et al. | ....... 424/1.45 |
| 6,677,329 B1 | * | 1/2004 | Loozen et al. | .............. 514/182 |

\* cited by examiner

*Primary Examiner*—Barbara P. Badio
(74) *Attorney, Agent, or Firm*—Weingarten, Schurgin, Gagnebin & Lebovici LLP

(57) ABSTRACT

The present invention comprises the design, synthesis and development of a new class of chemotherapeutic agents for prophylactic and therapeutic treatments in a mammal, particularly a human, believed to be at risk of suffering from a hormone-responsive disorde. In an embodiment of the invention, such treatments include therapeutic compositions comprising novel steroidal antiestrogen and antiandrogen compounds. In a preferred embodiment, such a novel compound of the present invention has an address and a message component, which are made into a single composite entity for more aggressive intervention and effective treatment of hormone-responsive disorders, thereby prolonging the disease-free interval for the patient and reducing a number of side effects.

2 Claims, 12 Drawing Sheets

STEROIDAL ANTIESTROGENS AND ANTIANDROGENS AND USES THEREOF

CROSS REFERENCE TO RELATED APPLICATIONS

This application is a 371 of PCT/US01/20142 filed Jun. 22, 2001 and claims the priority benefit of provisional U.S. patent application Ser. No. 60/213,282, filed Jun. 22, 2000 entitled, NOVEL STEROIDAL ANTIANDROGENS AND USES THEREOF, the whole of which is hereby incorporated herein by reference.

STATEMENT REGARDING FEDERALLY SPONSORED RESEARCH OR DEVELOPMENT

Part of the work leading to this invention was carried out with United States Government support provided under a grant from the National Institutes of Health, Contract Number 1R01CA81409. Therefore, the United States Government has certain rights in this invention.

BACKGROUND OF THE INVENTION

Antagonists to both estrogen and androgen receptors have been developed for the treatment of hormone-related conditions. For example, antiestrogenic agents are useful for the treatment of breast cancer and antiandrogenic agents are useful for the treatment of prostate cancer.

Breast cancer, at 182,000 cases per year, is the most common cancer diagnosis among women in the United States, accounting for over 40,000 deaths annually (Greenlee, 2000). It is estimated that one in eight women will develop breast cancer during their lifetime and one in three of those will die from the disease. Of those women diagnosed with breast cancer, approximately 60% have tumors that are classified as hormone-responsive, meaning that the tissue contains elevated levels of the estrogen receptor and the tumor cell proliferation is stimulated by circulating estrogens (Scott, 1991). Various available treatments include surgery (e.g., lumpectomy, mastectomy or modified radical mastectomy, which removes the breast and underlying muscle along with adjacent lymph nodes), radiation, chemotherapy or biological treatments.

Hormonal therapy characterized as either removal of estrogen producing tissues, inhibition of estrogen biosynthesis or blockade of estrogen receptors by antagonists (e.g., tamoxifen (Nolvadex®) and Faslodex®, raloxifene, and idoxifene), has been shown to produce a positive objective response (Beatson, 1896; Boyd 1900; Bhatanagar, 1999; Cole, 1971; and Lancet 351, 1998). Such interventions, however, are often accompanied by major side effects that are tolerated because of the particular risks associated with the primary disease. Over the past 10 years, studies with antiestrogens structurally related to tamoxifen have demonstrated that some of the side effects can be ameliorated, depending upon the features incorporated within the structure of the drug. Agents that may block cancer cell proliferation (antagonism) without eliminating the beneficial effects on bone density and cardioprotection have been termed Selective Estrogen Receptor Modulators (SERMs) (Grese; Levenson, 1999). Known non-steroidal antagonists that are tamoxifen-like and raloxifen-like display antiestrogen effects in some tissues and estrogen-like effects in others. These SERMs may be beneficial for the treatment of hormone responsive cancers (or potentially as prophylactic agents) without causing osteoporosis or increasing the risk for cardiovascular disease. However, their receptor affinity is generally less than that of estradiol, and because they have a non-steroidal structure, they often exhibit additional, non-hormonal effects. Additionally, hormone responsive cancers progress to a stage where they become hormone-independent, requiring a subsequent, more aggressive approach.

Prostate cancer is the most common cancer diagnosis among American men (29%) and the second leading cause of death due to cancer (13%) (Landis, 1999; Haas, 1997; Mettlin, 1997). Like breast cancer in women, most of the newly diagnosed cases are hormone responsive and patients experience a reduction in tumor growth or regression with antihormone (antiandrogen) therapy (Roach, 1999).

Hormonal therapy is often used in all phases of prostate cancer treatment to help block production or action of the male hormones that have been shown to fuel prostate cancer. Antiandrogens are divided into two groups: steroidal and non-steroidal. Among widely used approved hormone blockers, often used in combination, are Casodex (bicalutamide), Eulexin (flutamide), Anandron (nilutamide), LG 120907, which are nonsteroidal (see FIG. 9), and Lupron (leuprolide acetate), and Zoladex (goserelin acetate implant), which are peptides that block GnRH release. The nonsteroidal antiandrogens can be displaced by endogenous ligands, i.e., dihydrotestosterone. Therefore, these antiandrogens have not been as successful in the treatment of prostate cancer due to their reversability in binding to the androgen receptor. Some studies have suggested that dihydrotestosterone bromoacetate (DHT-BA) binds irreversibly to the androgen receptor (AR). However, other studies show that DHT-BA apparently binds to aldehyde dehydrogenase and not to the AR (McCammon, 1993). Therefore, DHT-BA is not as optimal in the treatment of prostate cancer.

Because the testicles produce male hormones, some men also undergo testicle removal to cut off the hormone supply. Advanced prostate cancer patients are usually treated with any number of chemotherapeutic drugs such as Novantrone (mitoxantrone), which do not cure the disease but often do ease pain and other symptoms. However, within one to three years of such therapy, there is often recurrence of disease in which the tumor has acquired hormone independence (Galbraith, 1997). At this point, antiandrogen therapy becomes much less effective and a more aggressive intervention is required (Ornstein, 1999). A second issue is that current antiandrogen therapy, even when effective, elicits a number of side effects (e.g., impotence, incontinence, loss of libido, gynecomastia, heat intolerance, or hot flashes) that compromise the patient's quality of life.

Therefore, the development of more therapeutically effective antiestrogenic and antiandrogenic agents that target hormone-dependent tumors would: (1) provide a substantial benefit for the initial reduction of disease, (2) provide a prolonged disease-free interval, (3) improve the long term prognosis, and (4) reduce the incidence and severity of the side effects.

BRIEF SUMMARY OF THE INVENTION

The present invention encompasses both prophylactic and therapeutic treatments for a mammal, preferably a human, at risk for a hormone-responsive disorder. In particular, the therapeutic compounds, compositions and methods of the present invention are directed to treatments for both existing estrogen- and androgen-mediated disorders and prevention thereof. Such disorders include, but are not limited to, prevention or treatment of osteoporosis, endometriosis, breast cancer, benign breast cancer, uterine cancer, ovarian cancer, polycystic ovarian disease, prostate cancer, benign prostatic hyperplasia (BPH), reduction of cardiac diseases, acne, seborrhea, alopecia, hirsutism, male pattern baldness, and infertility.

An embodiment of the therapeutic compound according to the invention is an antiestrogen compound having the structural formula, in the address/message construct described below:

a) an address unit having the structure:

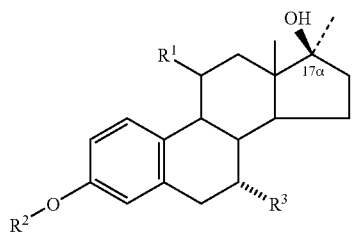

wherein:
$R^1$ is H, $CH_3$, $CH_2CH_3$, OH, $OCH_3$, $OCH_2CH_3$, $C_1$-$C_6$ alkyl, $CH=CH_2$, $CH=CHCH_3$, $CH_2$-aryl;
$R^2$ is H, $CH_3$, $COCH_3$, $CO(CH_2)_nCH_3$, CO-aryl, alkyl, cycloalkyl (ether), ester, $-COCH_3$;
$R^3$ is $CH_3$, $CH_2CH_3$, aryl, heteroaryl, alkyl $C_1$-$C_6$, alkyl ($C_1$-$C_6$) amides, alkyl ($C_1$-$C_6$) sulfide, alkyl ($C_1$-$C_6$) sulfone, alkyl ($C_1$-$C_6$) sulfoxide;
$R^9$ is H, OH, $NH_2$; and, attached to the 17α-position of the address unit, b) a message unit having the structure:

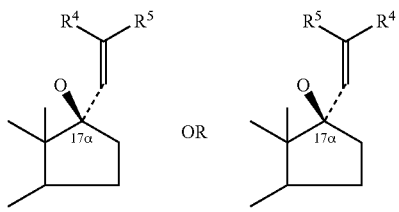

wherein:
$R^4$ is H, alkyl ($C_1$-$C_4$);
$R^5$ is aryl, heteroaryl, fused aryl, —CO-aryl, CO-fused aryl, —CO-heteroaryl, —CO-fused heteroaryl, biaryl, CO-biaryl, ether-linked aryls, ether-linked heteroaryls, amine-linked aryls, amine-linked heteroaryls, aminoalkoxy arene hybrid, peptidyl hybrid, wherein any aryl, heteroaryl, fused aryl, fused heteroaryl, biaryl, CO-biaryl, ether-linked aryls, ether-linked heteroaryls, amine-linked aryls, amine-linked heteroaryls, aminoalkoxy arene hybrid, and peptidyl hybrid as used herein for groups exemplified in Table 1, rows 13–15, may optionally be substituted, independently, with H, $CH_3$, OH, $OCH_3$, $OCF_3$, $NCH_3$, $NCOCH_3$, aryl, $CO_2CH_3$, $CONH_2$, $C_1$-$C_4$ alkyl, $(CF_2)_nF$ wherein n=1–4, Cl, Br, I, F, $O(CH_2)_nH$ wherein n=1–4, $NO_2$, $NH_2$, $NHCOR_1$, $CO_2H$, $CO_2R^4$, CONHR4, amyl, thioether, $SR^6$, $S(O)R^6$, $SO_2R^6$, $SO_2NR^6R^7$; wherein $R^6$ is H, $C_1$-$C_4$ alkyl or perfluoroalkyl, aryl, heteroaryl, or optionally substituted allyl, arylmethyl, alkynyl, alkenyl; wherein $R^7$ is H, $C_1$-$C_4$ alkyl or perfluoroalkyl, aryl, heteroaryl, optionally substituted allyl, arylmethyl, $OR^8$ or $NHR^8$; wherein $R^8$ is H, $C_1$-$C_6$ alkyl or perfluoroalkyl, aryl, heteroaryl, optionally substituted allyl or arylmethyl, $SO_2R^6$ or $S(O)R^6$, wherein $R^6$ has the definition given above; and wherein $R^5$ can be in either the E or Z configuration in relation to the 17α-position of the address unit.

Examples of the combined structural formula for the antiestrogen compounds of the present invention that includes both the address and the message units are as follows:

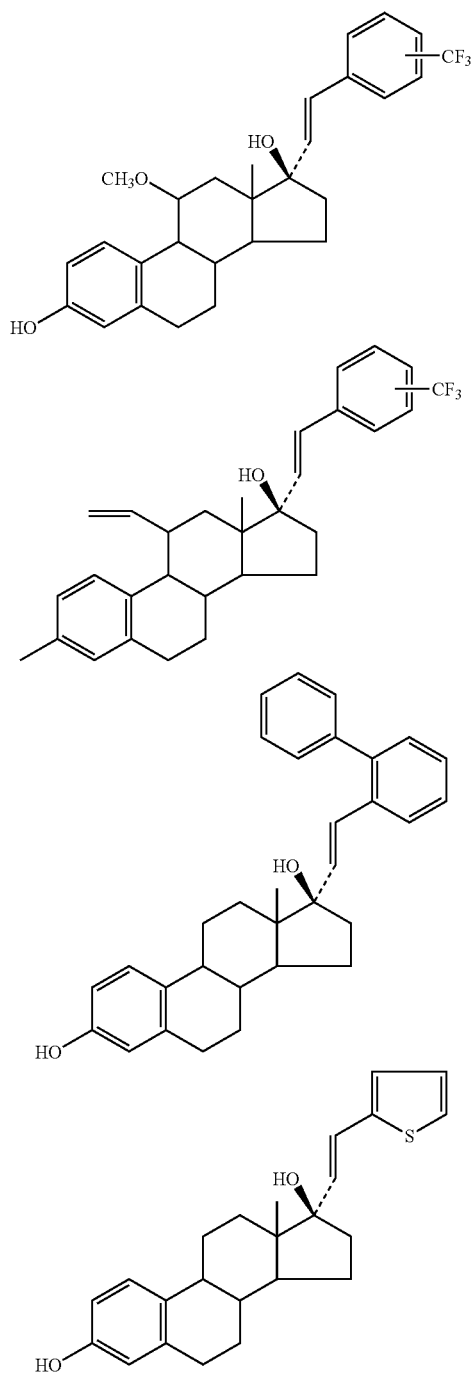

-continued

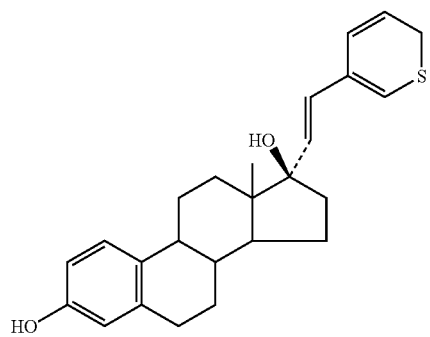

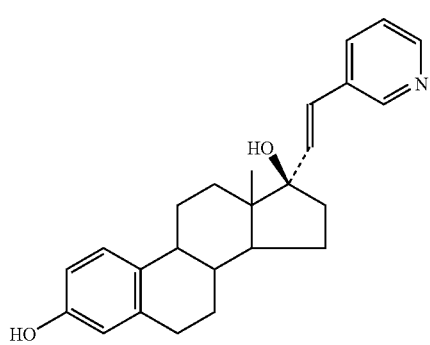

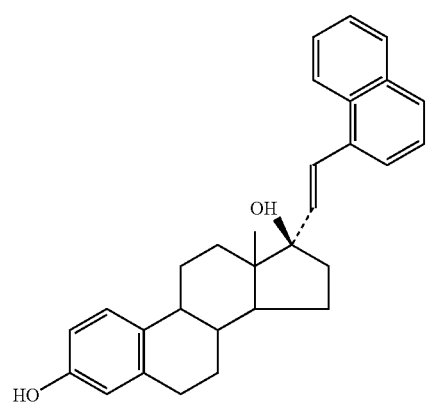

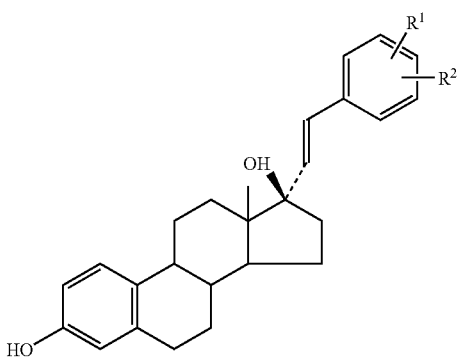

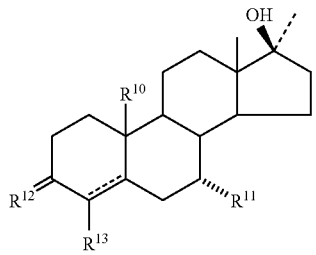

OR

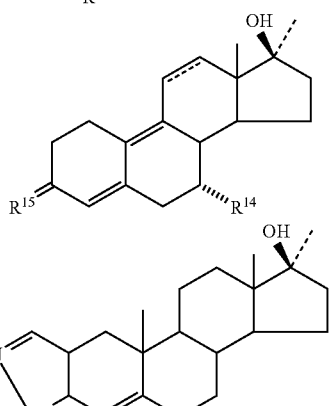

OR wherein:
R$^{10}$ is H, CH$_3$;
R$^{11}$ is H, C$_1$-C$_4$ alkyl;
R$^{12}$ is O, (H, OH);
R$^{13}$ is H, OH, Cl, Br, I, CH$_3$;
R$^{14}$ is H, C$_1$-C$_4$ alkyl;
R$^{15}$ is O, (H, OH);
R$^{16}$ is O, NH;
R$^{17}$ through R$^{18}$ each independently is H, CH$_3$; and, attached to the 17α-position of the address unit, and b) a message unit having the structure:

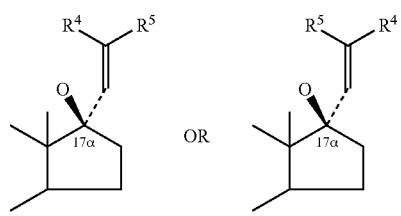

wherein:
R$^4$ is H, alkyl (C$_1$-C$_4$);
R$^5$ is aryl, heteroaryl, fused aryl, —CO-aryl, CO-fused aryl, —CO-heteroaryl, —CO-fused heteroaryl, biaryl, CO-biaryl, ether-linked aryls, ether-linked heteroaryls, amine- In another embodiment, the present invention is directed to antiandrogen compounds having the structural formula, in the address/message construct described below:

a) an address unit having one of the following different structures:

linked aryls, amine-linked heteroaryls, wherein any aryl, heteroaryl, fused aryl, fused heteroaryl, biaryl, CO-biaryl, ether-linked aryls, ether-linked heteroaryls, amine-linked aryls, and amine-linked heteroaryls may optionally be substituted, independently, with H, $CH_3$, OH, $OCH_3$, $OCF_3$, $NCH_3$, $NCOCH_3$, aryl, $CO_2CH_3$, $CONH_2$, $C_1$-$C_4$ alkyl, $(CF_2)_nF$ wherein n=1–4, Cl, Br, I, F, $O(CH_2)_nH$ wherein n=1–4, $NO_2$, $NH_2$, $NHCOR^4$, $CO_2H$, $CO_2R^4$, $CONHR^4$, amyl, thioether, $SR^6$, $S(O)R^6$, $SO_2R^6$, $SO_2NR^6R^7$; wherein $R^4$ has the definition given above; wherein $R^6$ is H, $C_1$-$C_4$ alkyl or perfluoroalkyl, aryl, heteroaryl, or optionally substituted allyl, arylmethyl, alkynyl, alkenyl; wherein $R^7$ is H, $C_1$-$C_4$ alkyl or perfluoroalkyl, aryl, heteroaryl, optionally substituted allyl, arylmethyl, $OR^8$ or $NHR^8$; wherein $R^8$ is H, $C_1$-$C_6$ alkyl or perfluoroalkyl, aryl, heteroaryl, optionally substituted allyl or arylmethyl, $SO_2R^6$ or $S(O)R^6$, wherein $R^6$ has the definition given above; and wherein $R^5$ can be in either the E or Z configuration in relation to the 17α-position of the address unit.

Exemplary antiandrogen compounds containing both the address and the message units are as follows:

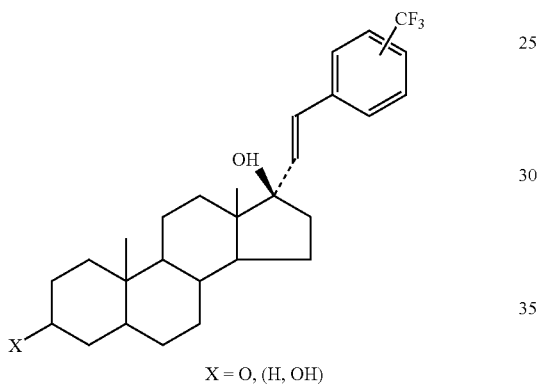

X = O, (H, OH)

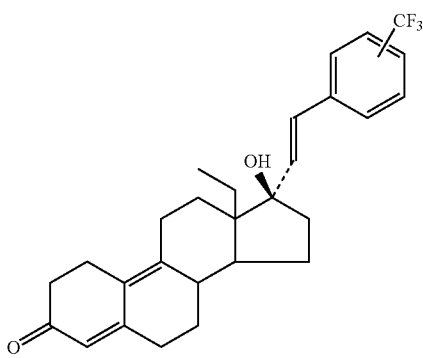

-continued

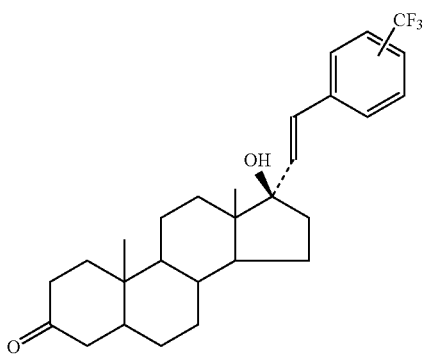

Exemplary $R^5$ groups of the present invention are as follows:

TABLE 1

EXEMPLARY $R^5$ GROUPS

| 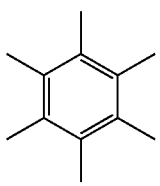 | 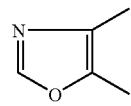 |
|---|---|
|  |  |
| 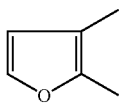 | 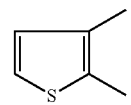 |
| 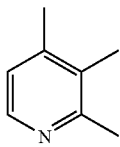 |  |

TABLE 1-continued
EXEMPLARY R⁵ GROUPS
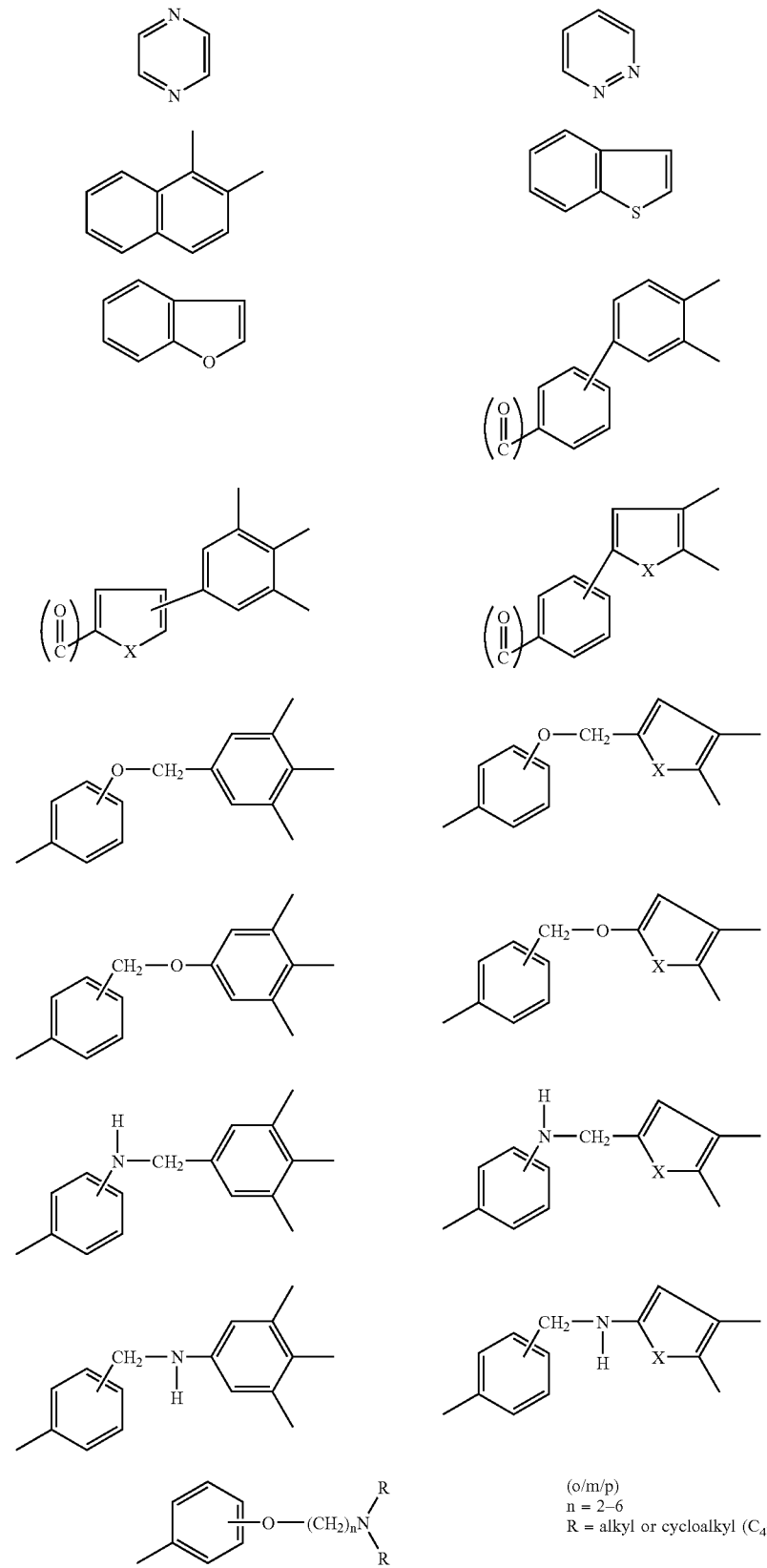
(o/m/p)
n = 2–6
R = alkyl or cycloalkyl (C₄–C₈)

TABLE 1-continued

EXEMPLARY $R^5$ GROUPS

| Structure | Notes |
|---|---|
| ![structure with $CH_2N-(CO-CHNH)_n H$, R on CH] | (o/m/p) amide bond L or D<br>n = 1–4<br>R = alkyl or cycloalkyl ($C_4$–$C_8$) |
| ![structure with $(CH_2)_n-CO-(NH-CHR-CO)_m-NH-CHR-CO-OH$] | (o/m/p) amide bond L or D<br>n = 0–2<br>m = 0–3<br>R = alkyl or cycloalkyl ($C_4$–$C_8$) |

The above exemplary structures can be substituted at above. Any aryl and heteroaryl groups can be substituted with one to five substituent groups, preferably one to three substituent groups. These substituent groups may include, independently, H, $CH_3$, OH, $OCH_3$, $OCF_3$, $NCH_3$, $NCOCH_3$, aryl, $CO_2CH_3$, $CONH_2$, $C_1$-$C_4$ alkyl, $(CF_2)_nF$ wherein n=1–4, Cl, Br, I, F, $O(CH_2)_nH$ wherein n=1–4, $NO_2$, $NH_2$, NHCOR, $CO_2H$, $CO_2R^4$, $CONHR^4$, amyl, thioether, $SR^6$, $S(O)R^6$, $SO_2R^6$, $SO_2NR^6R^7$; wherein $R^4$ has the definition given above; wherein $R^6$ is H, $C_1$-$C_4$ alkyl or perfluoroalkyl, aryl, heteroaryl, or optionally substituted allyl, arylmethyl, alkynyl, alkenyl; wherein $R^7$ is H, $C_1$-$C_4$ alkyl or perfluoroalkyl, aryl, heteroaryl, optionally substituted allyl, arylmethyl, $OR^8$ or $NHR^8$; wherein $R^8$ is H, $C_1$-$C_6$ alkyl or perfluoroalkyl, aryl, heteroaryl, optionally substituted allyl or arylmethyl, $SO_2R_6$ or $S(O)R^6$, wherein $R^6$ has the definition given above; and wherein $R^5$ can be in either the E or Z configuration.

Any aryl and heteroaryl groups with any combinations thereof for the compounds of the present invention can be substituted as elsewhere described, with one to five substituent groups. In a preferred embodiment, any aryl and heteroaryl groups with any combinations thereof can be substituted as elsewhere described with one to three substituent groups, where the preferred substituent positions are indicated elsewhere herein.

These compounds are capable of effectively binding to the estrogen or the androgen receptor, accordingly, to inhibit or modulate the actions of either estrogens or androgens.

In another embodiment, the present invention is directed to a therapeutic composition for prophylaxis or treatment of a hormone-responsive disorder containing the antiestrogenic and antiandrogenic compounds described above. The therapeutic composition is contained in a pharmaceutically acceptable inert carrier substance that is formulated for oral, topical, intravenous, intramuscular, subcutaneous, intravaginal, suppository or parental administration.

In another embodiment, the present invention is directed to a method of treating a patient suffering from or believed to be at risk of suffering from a hormone-responsive disorder by administering to the patient an effective amount of any of the therapeutic compositions described above for preventing or treating hormone-responsive disorders.

In a further embodiment, the therapeutic compositions of the present invention comprising the antiestrogen/antiandrogen compounds can be administered, if a low dosage is preferred, in a dosage of about 0.1 µg/kg (body weight) per day to 10 µg/kg/day, preferably 0.5 µg/kg/day to 5 µg/kg/day, and preferably 1 µg to 100 µg for local administration.

An exemplary preferred high dosage amount may be in the range of about 0.10 mg/kg/day to about 40 mg/kg/day, more preferably of about 0.50 mg/kg/day to about 20 mg/kg/day, and more preferably of about 1.0 mg/kg/day to about 10 mg/kg/day. Optimal dosage and modes of administration can readily be determined by conventional protocols. The amount of administration is also dependent on the disease-state, on the patient being treated, the patient's body weight and the type of administration.

In a further embodiment, the present invention is directed to a kit comprising a therapeutic composition as described above and instructions for use thereof.

In a particular embodiment, the present invention is directed to a method for the prophylaxis or treatment of prostate disorders in a patient by administering an antiandrogenic compound described herein in an effective amount. While not being bound by any theory, it is believed that in particular, the antiandrogenic compounds of the invention change the structural conformation in the helix-12 of the androgen receptor to inhibit transcriptional response.

In another embodiment, the present invention is directed to an article of manufacture comprising a packaging material and a therapeutic composition of the present invention contained within the packaging material. The therapeutic composition is therapeutically effective for prophylactic or treatment of hormone-responsive disorders. The packing material also comprises a label with instructions for use, which indicates that the therapeutic composition can be used for phrophylaxis or treatment of hormone-responsive disorders.

BRIEF DESCRIPTION OF THE FIGURES

Other features and advantages of the invention will be apparent from the following description of the preferred embodiments thereof and from the claims, taken in conjunction with the accompanying drawings, in which:

Figure 2:
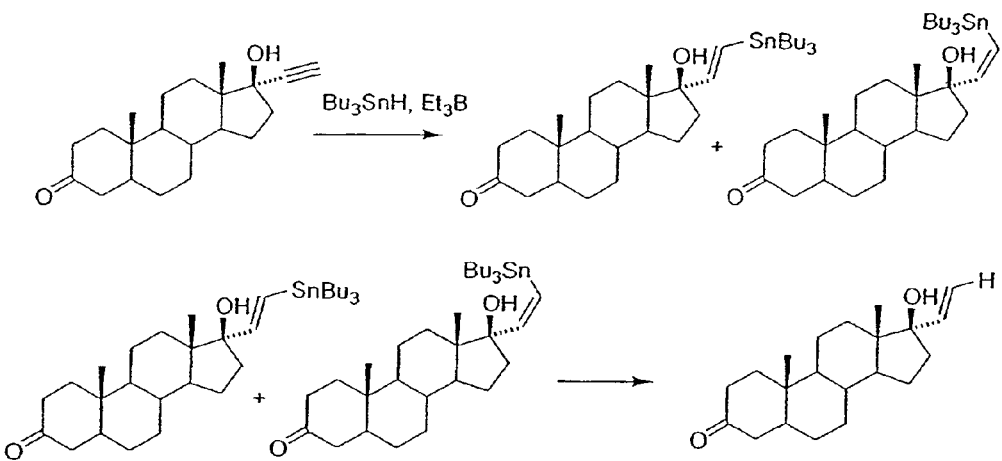
Figure 3:
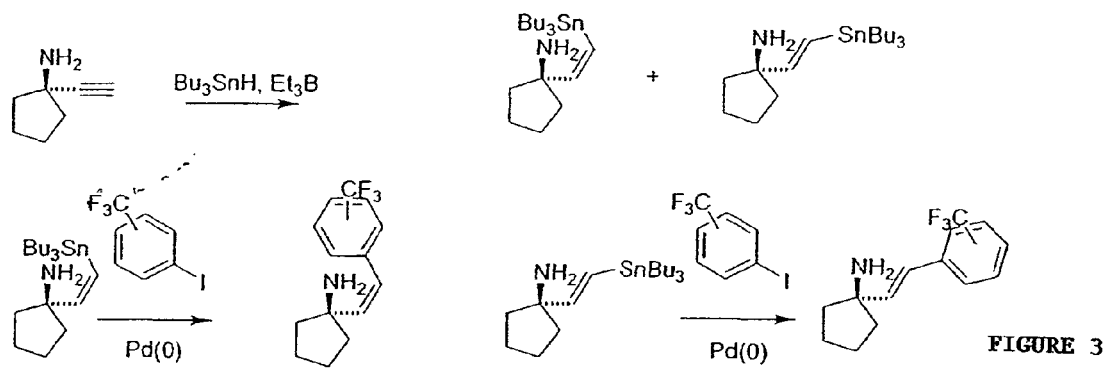
Figure 4:
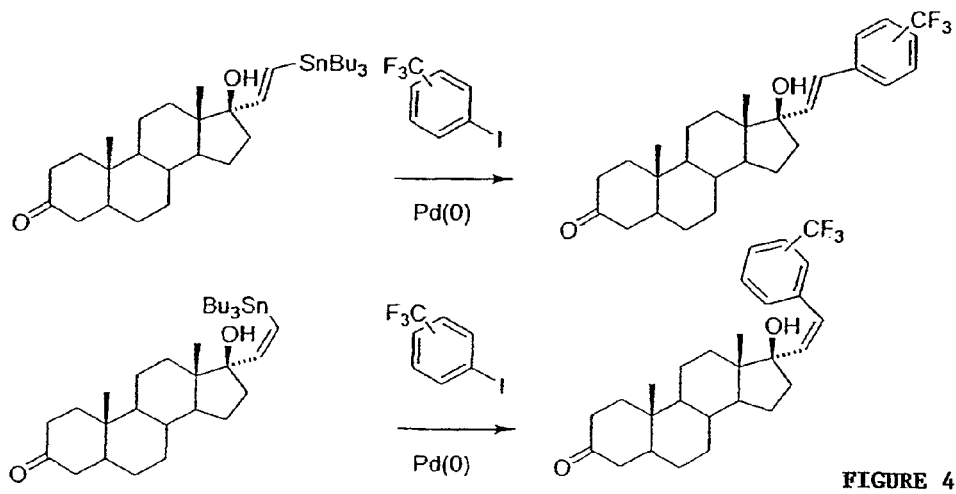
Figure 5:
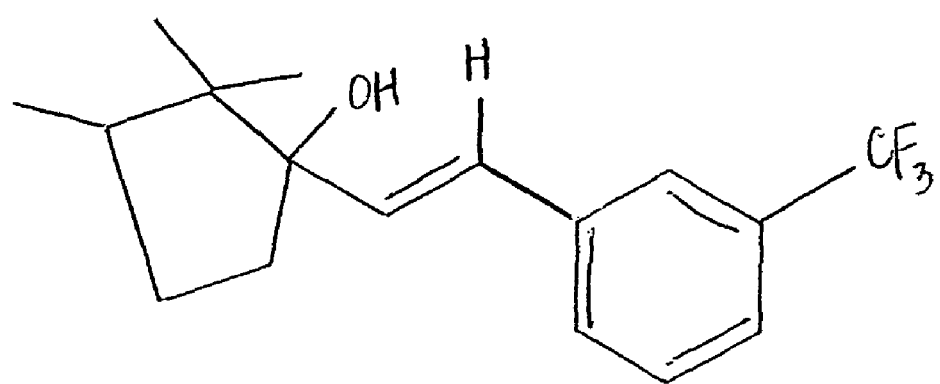
Figure 5:
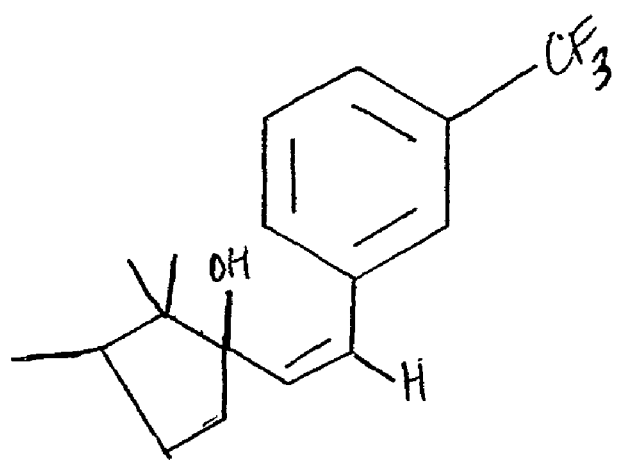
Figure 6:
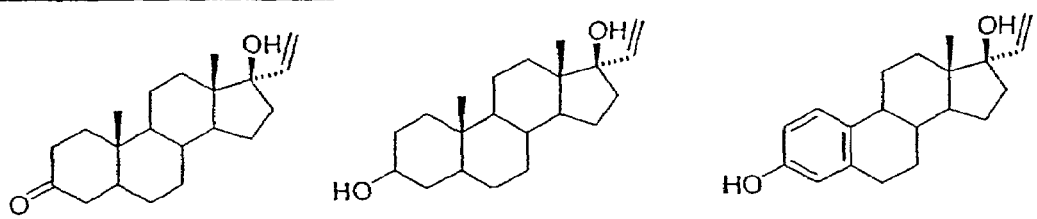
Figure 6:
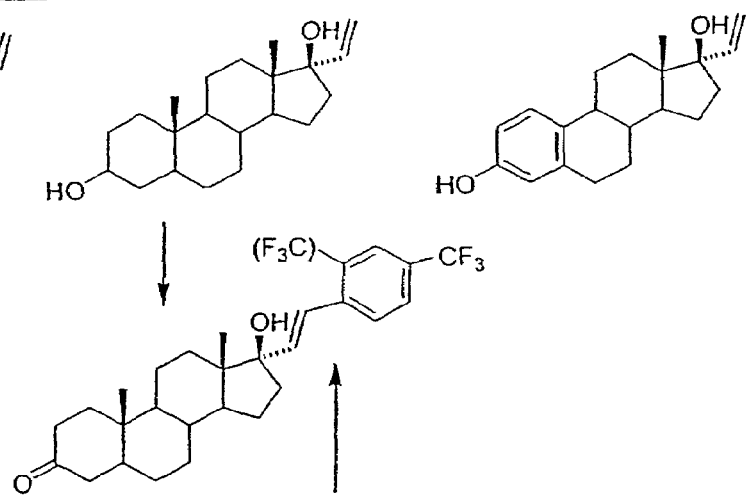
Figure 6:
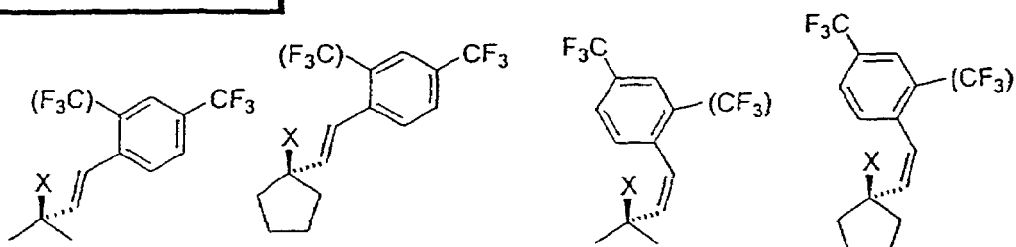
Figure 7:
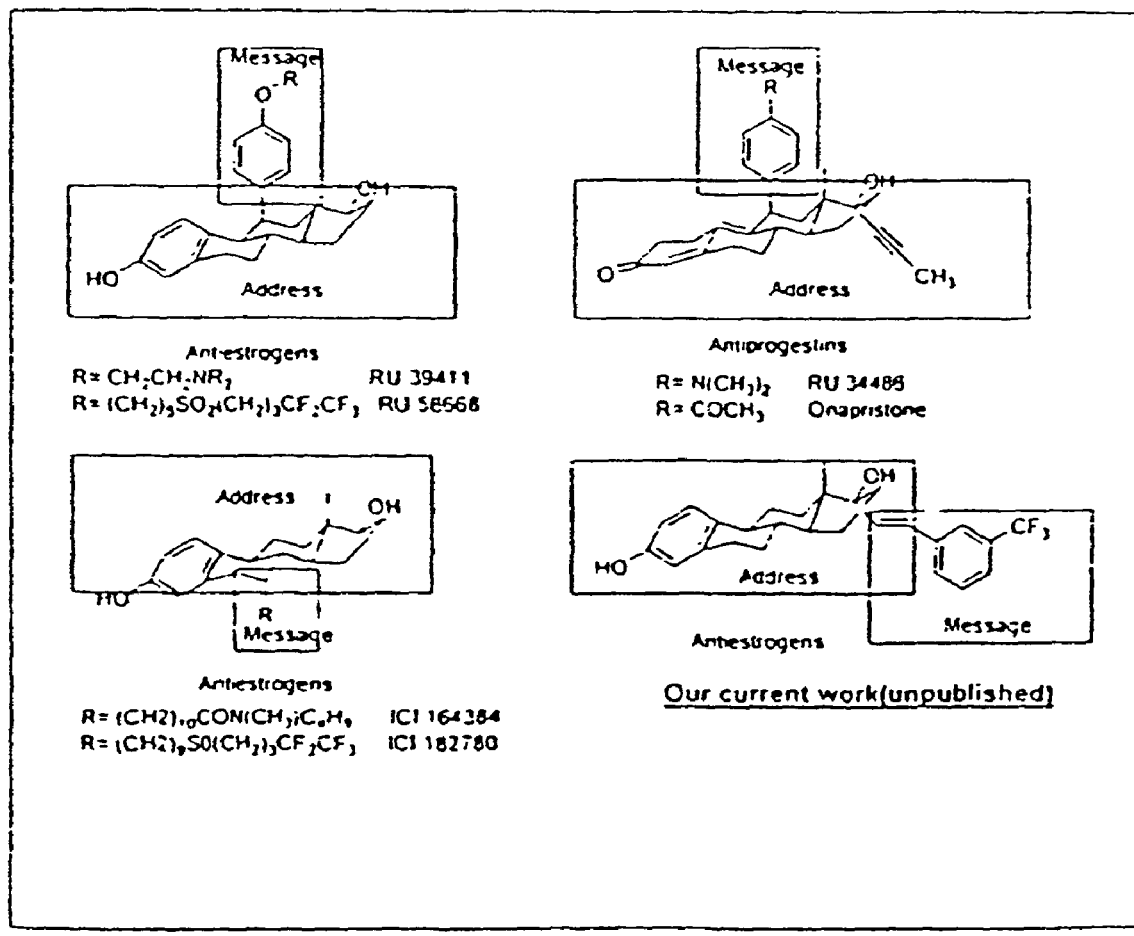
Figure 8:
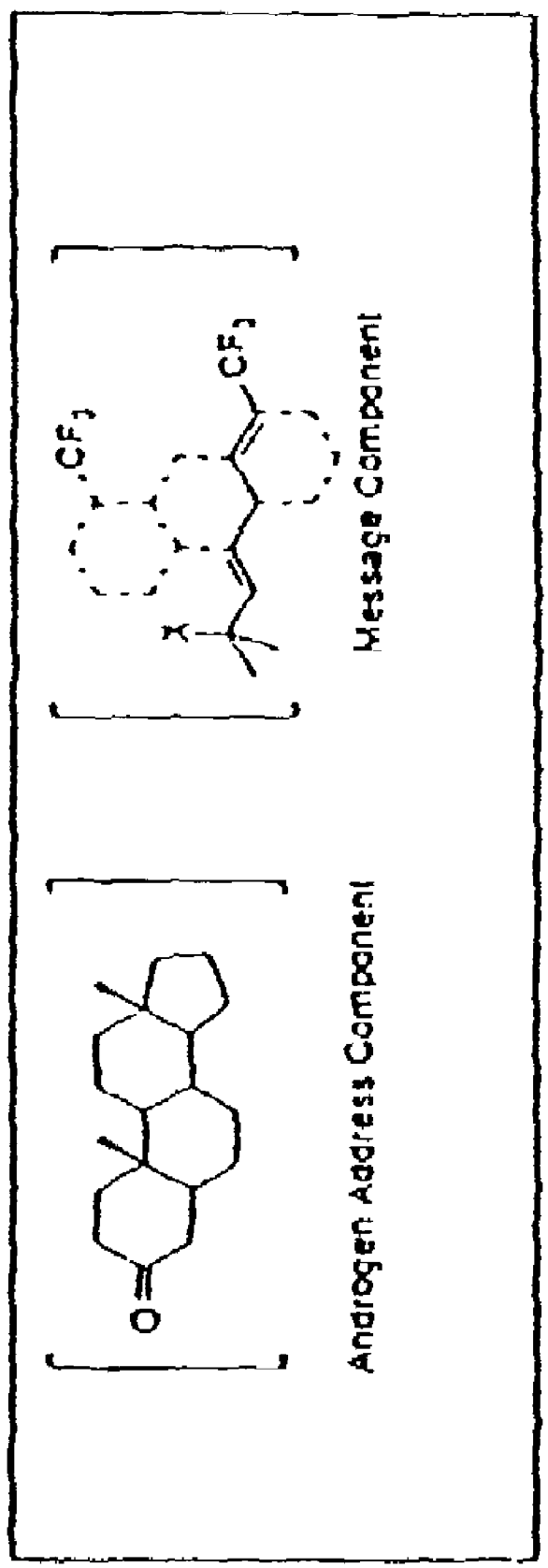
Figure 9:
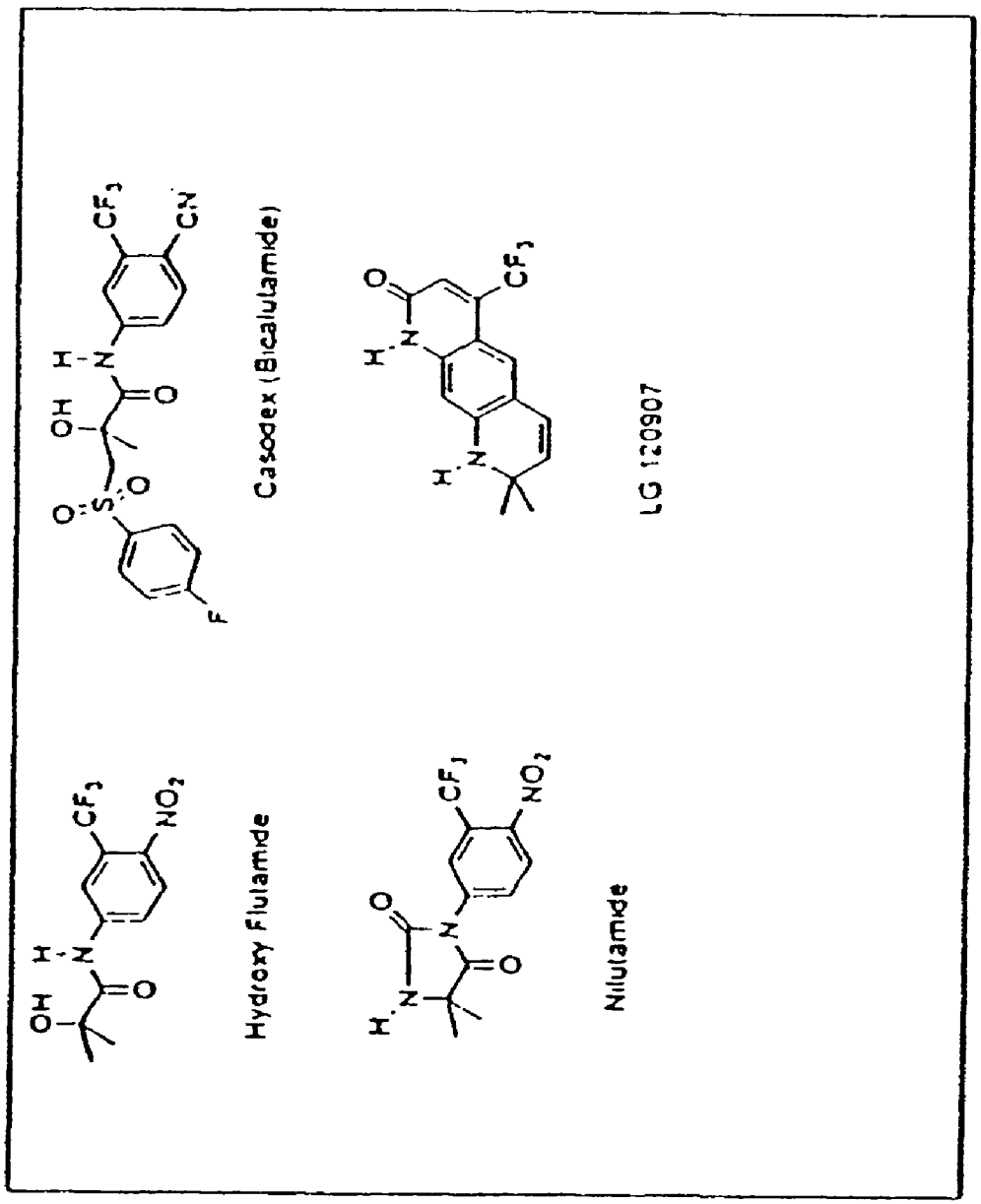
Figure 10:
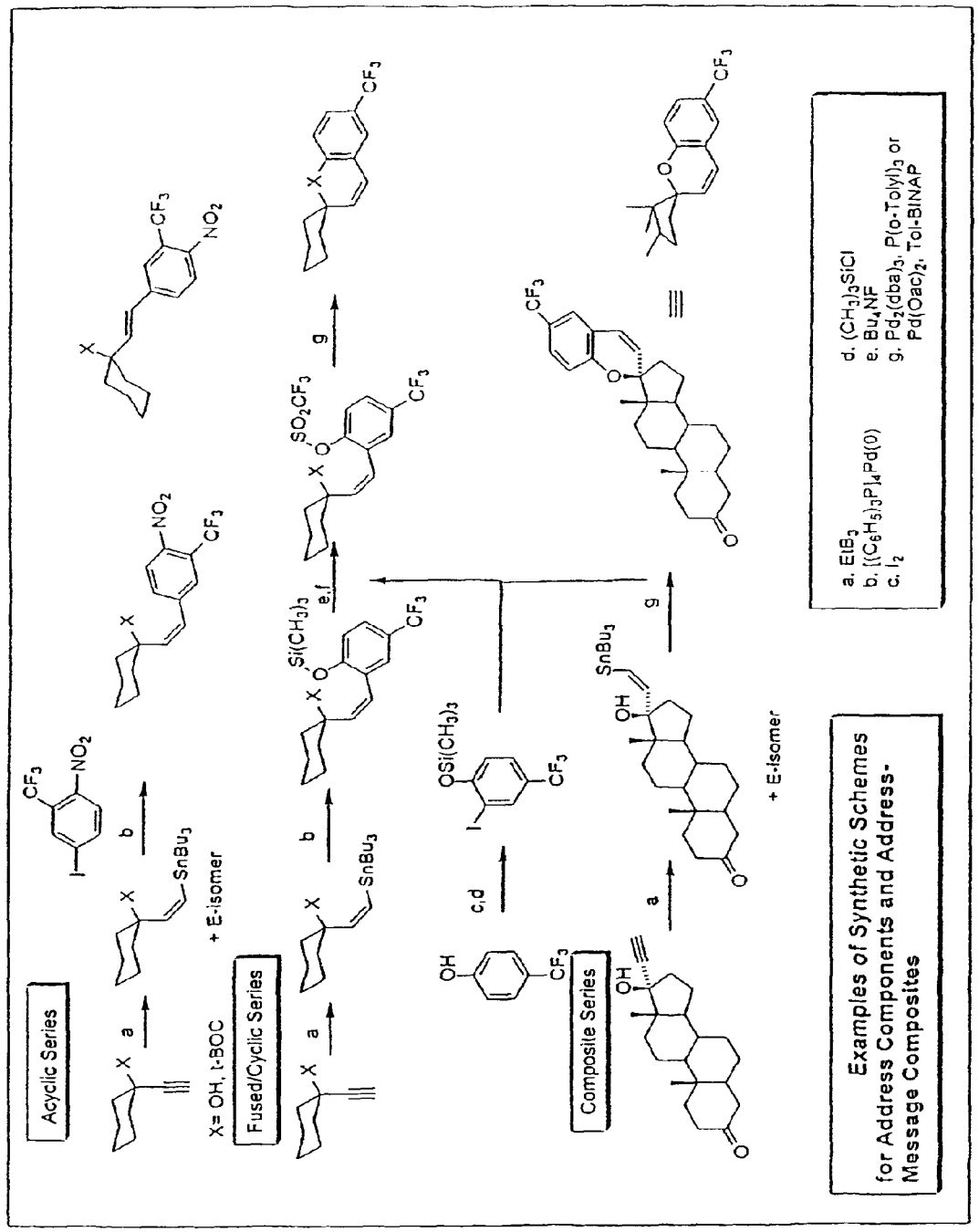
Figure 11:
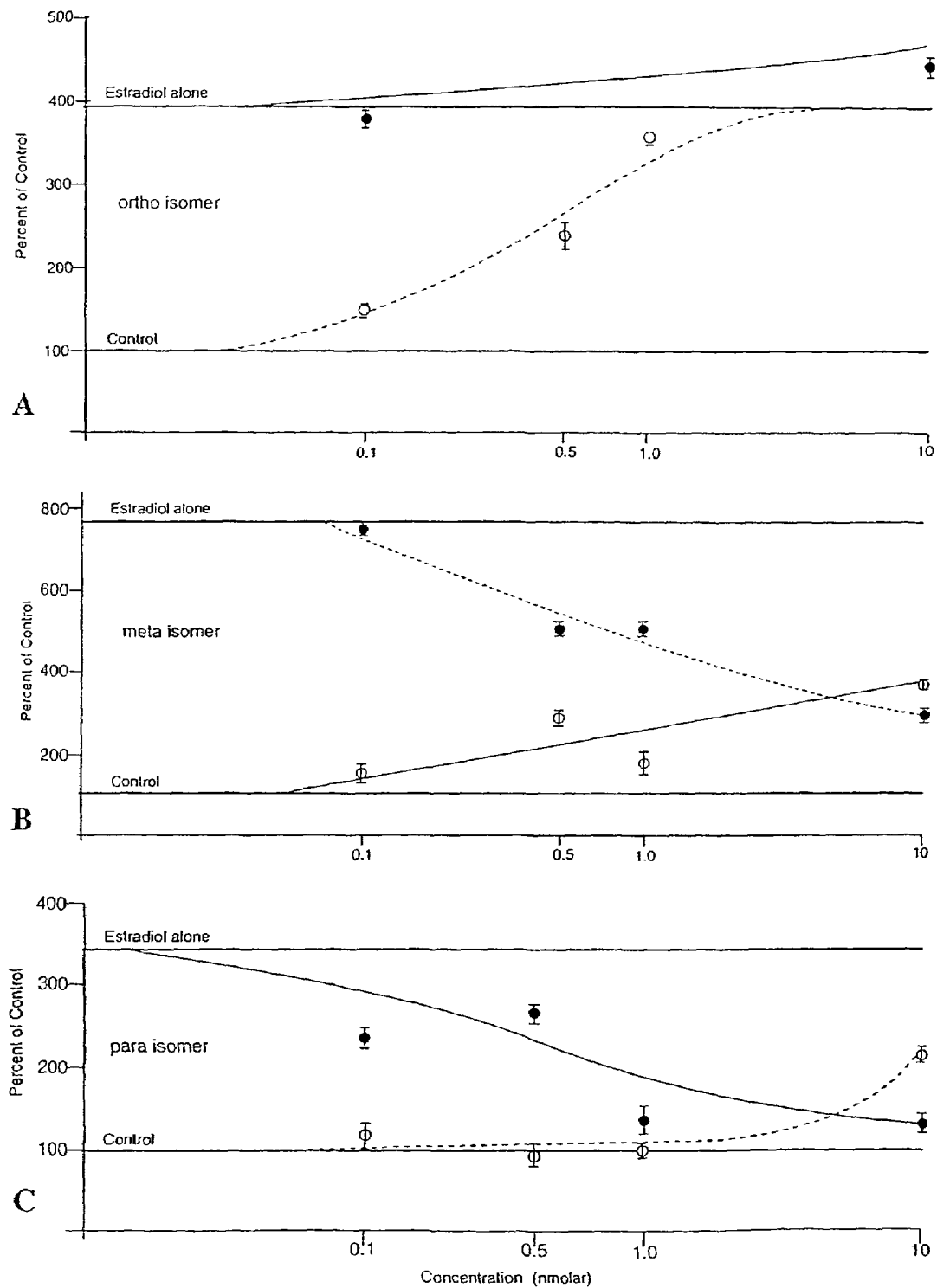
Figure 12:
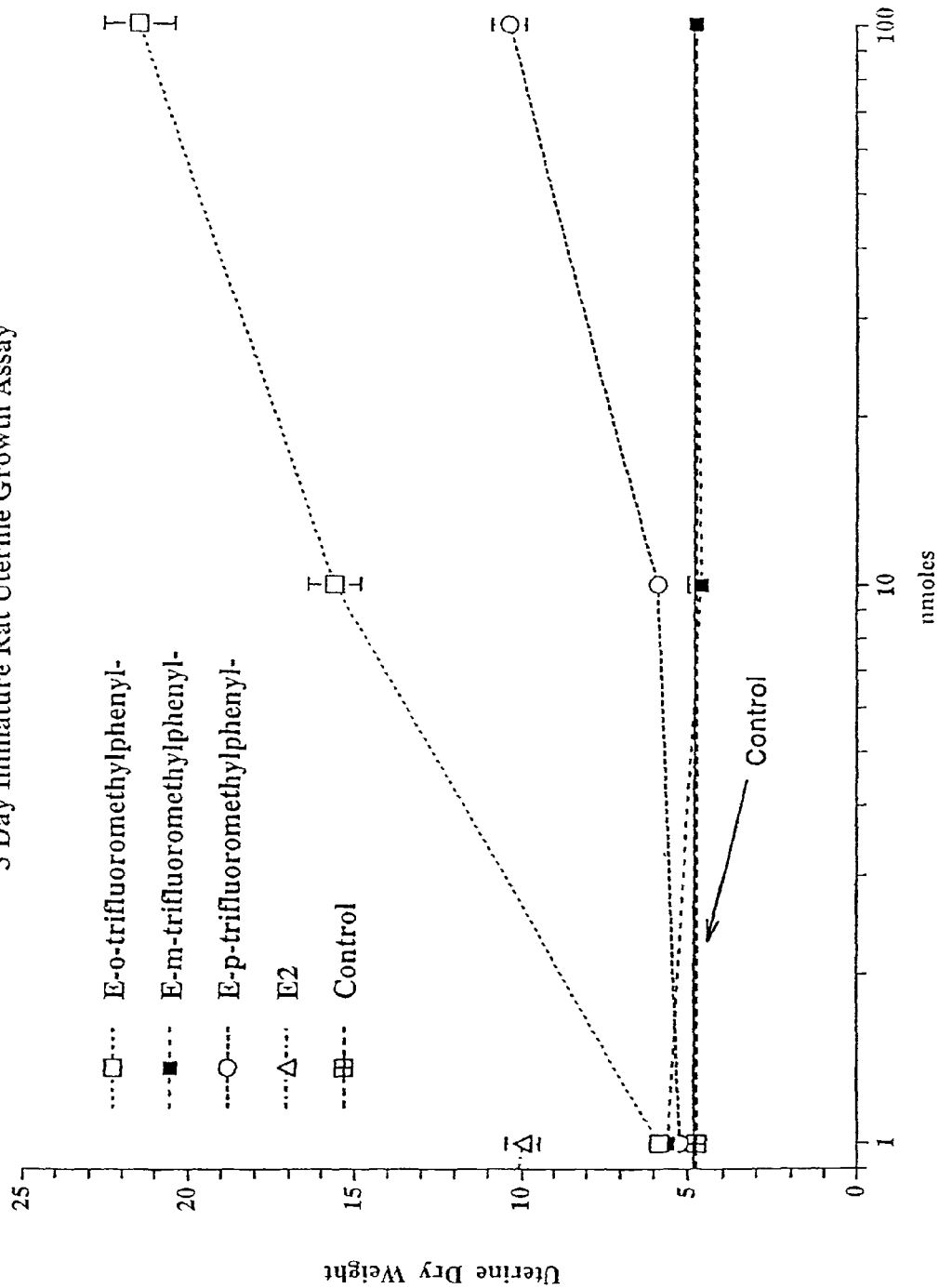
Figure 13:
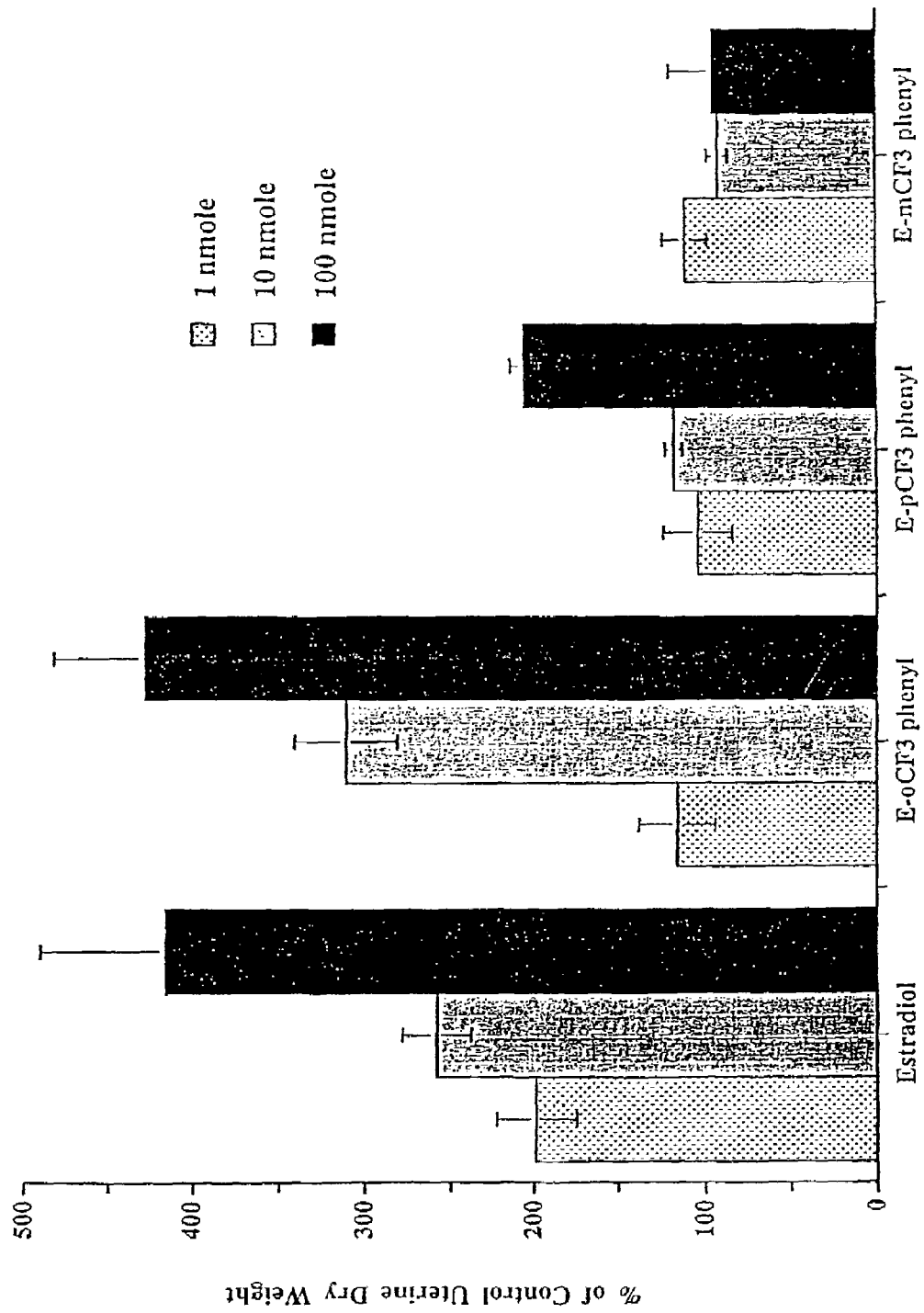
Figure 14:
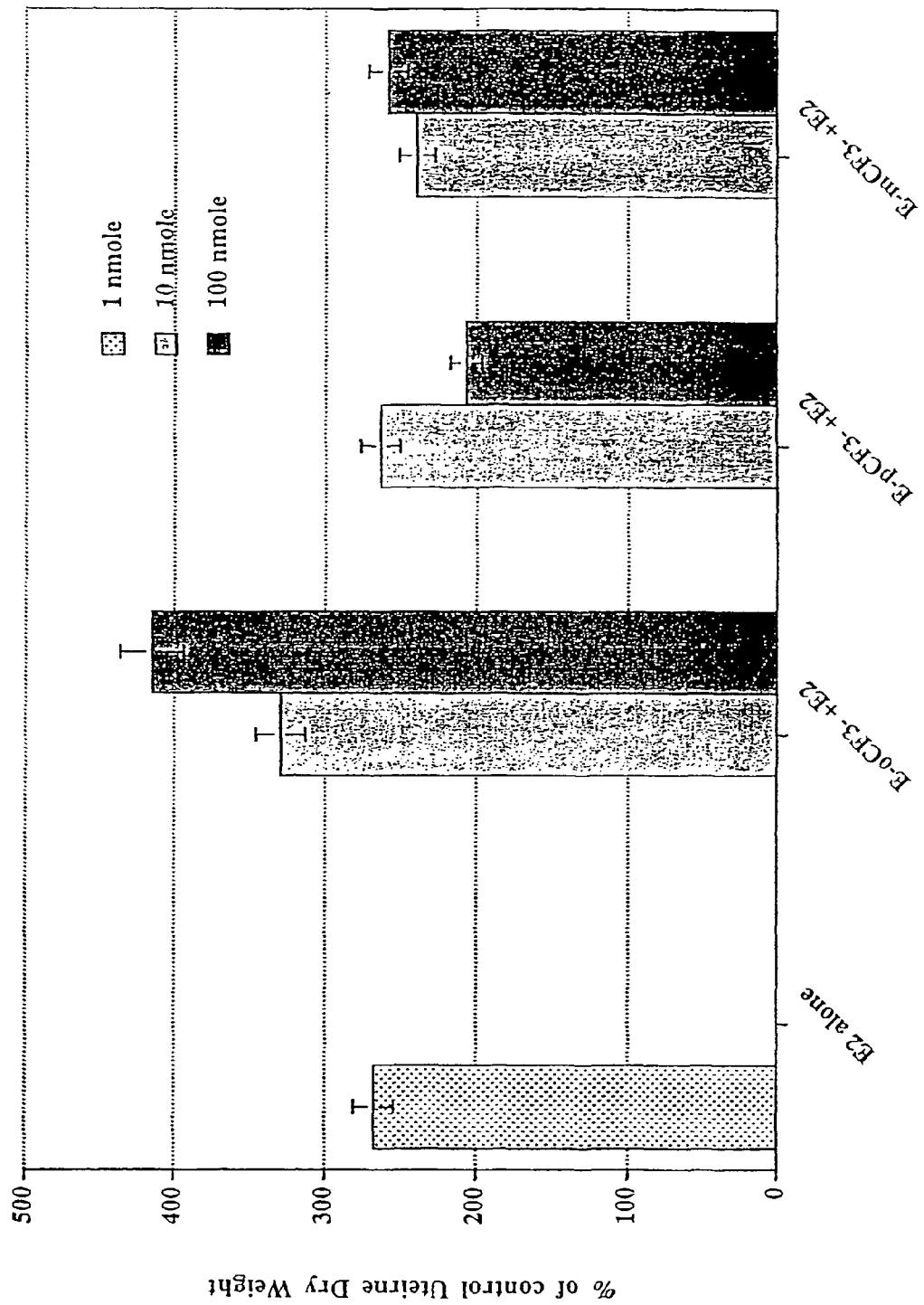

a—Jones reagent ($H_2Cr_2O_4$, $H_2SO_4$, acetone);
b—n-BuLi, TMEDA, cyclohexane, 50° C.;
c—Dry ice, THF;
d—17α-Ethynyl estradiol, DCC, DMAP, $CH_2Cl_2$;
e—HSnBU3, $Et_3B$, THF, 50–60° C.;
f—17α-Ethynyl estradiol, HSnBU3, $Et_3B$, THF, 50–60° C.;
g—DCC, DMAP, $CH_2Cl_2$;

h—R-Aryl-X, Pd(PPh$_3$)$_4$, BHT, toluene, N$_2$, reflux;
i—5 N-NaOH in CH$_3$OH-Dioxane (1:3);
j—5%-CH$_3$COOH;
k—10%-NaHCO$_3$;

FIG. 2 depicts the synthesis of an exemplary address unit;

FIG. 3 depicts the synthesis of an exemplary message unit;

FIG. 4 depicts the synthesis of an address-message combination;

FIG. 5 depicts the E and Z isomers of 3-(trifluoromethyl) phenylvinyl estradiol;

FIG. 6 depicts the exemplary composite of both the address and message units;

FIG. 7 depicts prior art antihormones that incorporate functional groups at the 11β- or 7α-position of the steroid nucleus;

FIG. 8 depicts exemplary steroid nucleus (address component) and the nonsteroidal antagonist pharmacophore (message component);

FIG. 9 depicts prior art nonsteroidal ligands with antiandrogen message component (Helix-12 modulators);

FIG. 10 depicts the synthesis of message components using a modified combination of organotin chemistry and palladium-catalyzed coupling reactions;

FIGS. 11a–11c are graphs depicting the results of proliferation assays of MCF-7 cells with (ortho, meta, or para) 3-(trifluoromethyl)phenylvinyl estradiol;

FIG. 12 is a graph depicting the results of a three-day immature female rat uterotrophic growth assay with (ortho, meta, or para) 3-(trifluoromethyl)phenylvinyl estradiol;

FIG. 13 is a graph depicting the results of the estrogenicity of 17α-(ortho, meta, or para) 3-(trifluoromethyl) phenylvinyl estradiols in the immature female rat; and FIG. 14 is a graph depicting the results of an antiestrogen assay of 17α-(ortho, meta, or para) 3-(trifluoromethyl)phenylvinyl estradiols in the immature female rat.

DETAILED DESCRIPTION OF THE INVENTION

Definition of Terms

The term "alkyl" used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain 1 to 12 carbon atoms. The term "lower alkyl" intends an alkyl group of one to six carbon atoms, preferably one to four carbon atoms. The term "cycloalkyl" intends a cyclic alkyl group, typically of 3 to 6 carbon atoms, more preferably 4 to 5 carbon atoms. The term "cyclooxyalkyl" intends a cyclic alkyl group containing a single ether linkage, again, typically containing 3 to 6 carbon atoms, more preferably 4 to 5 carbon atoms.

The term "aryl" as used herein refers to a monocyclic aromatic species of 5 to 7 carbon atoms, and is typically phenyl. Optionally, these groups are substituted with one to five, more preferably one to three, lower alkyl, lower flouroalkyl, lower alkoxy, halo, nitro, amino, amide, carboxy, thioether, sulfide, sulfoxide, sulfamino, and/or sulfamide substituents. The aryl group may also comprise of di-, tri-, hexa-, penta-substituted phenyl with all positional (ortho, meta, para) variations. The term "lower flouroalkyl" intends an alkyl group of one to six carbon atoms, preferably one to four carbon atoms. The term "lower alkoxy" intends an alkoxy group with one to six carbon atoms, preferably one to four carbon atoms. The term "carboxy aryl" as used herein refers to a carboxy group attached to the aryl group.

The term "halo" or "halogen" refers to fluoro, chloro, bromo or iodo, and usually relates to halo substitution for a hydrogen atom in an organic compound.

The term "optional" or "optionally" means that the subsequently described event or circumstance may or may not occur, and that the description includes instances where said event or circumstance occurs and instances where it does not.

The term "heteroaryl" as used herein refers to monocyclic aromatic species of three to seven carbon atoms, and is preferably one to six carbon atoms, and is more preferably one to five carbon atoms, and is typically phenyl. In particular, the heteroaryl comprises, for example, oxazole, thiazole, isoxazole, where these heteroaryls have nitrogen, oxygen, or sulfur atoms in the monocyclic ring. Optionally, these groups are substituted with one to five, more preferably one to three, lower alkyl, lower flouroalkyl, lower alkoxy, halo, nitro, amino, amide, carboxy, thioether, sulfide, sulfoxide, sulfamino, and/or sulfamide substituents. The aryl group may also comprise of di-, tri-, hexa-, penta-substituted phenyl with all positional (ortho, meta, para) variations. The term "carboxy-heteroaryl" as used herein refers to a carboxy group attached to a heteroaryl group.

The term "fused aryl" as used herein refers to bicyclic aromatic species of three to seven carbon atoms, and is typically phenyl. In particular, the fused aryl may comprise of naphthyl, benzothienyl, or benzofuryl. Optionally, these groups are substituted with one to five, more preferably one to three, lower alkyl, lower flouroalkyl, lower alkoxy, halo, nitro, amino, amide, carboxy, thioether, sulfide, sulfoxide, sulfamino, and/or sulfamide substituents. The aryl group may also comprise of di-, tri-, hexa-, penta-substituted phenyl with all positional (ortho, meta, para) variations. The term "carboxy-fused aryl" as used herein refers to a carboxy group attached to a fused-aryl group.

The term "biaryl" as used herein refers to two monocyclic aromatic species of four to seven carbon atoms, and is typically different configurations of a combination of a phenyl and a heteroaryl. Optionally, these groups are substituted with one to five, more preferably one to three, lower alkyl, lower flouroalkyl, lower alkoxy, halo, nitro, amino, amide, carboxy, thioether, sulfide, sulfoxide, sulfamino, and/ or sulfamide substituents. The aryl group may also comprise of di-, tri-, hexa-, penta-substituted phenyl with all positional (ortho, meta, para) variations. The term "carboxy-biaryl" as used herein refers to a biaryl attached to a carboxy group.

The terms "ether-linked aryls" and "ether-linked heteroaryls" as used herein refer to two aryls/heteroaryls as defined above that are linked by an ether group. Optionally, these groups are substituted with one to five, more preferably one to three, lower alkyl, lower flouroalkyl, lower alkoxy, halo, nitro, amino, amide, carboxy, thioether, sulfide, sulfoxide, sulfamino, and/or sulfamide substituents. The aryl group may also comprise of di-, tri-, hexa-, penta-substituted phenyl with all positional (ortho, meta, para) variations.

The terms "amine-linked aryls" and "amine-linked heteroaryls" as used herein refer to two aryls/heteroaryls as defined above that are linked by an amine group. The terms aminoalkoxyl arene hybrids and peptidyl hybrids as used herein are referred to the groups exemplified in Table 1. Optionally, these groups are substituted with one to five, more preferably one to three, lower alkyl, lower flouroalkyl, lower alkoxy, halo, nitro, amino, amide, carboxy, thioether, sulfide, sulfoxide, sulfamino, and/or sulfamide substituents.

Aryl group may also comprise of di-, tri-, hexa-, penta-substituted phenyl with all positional (ortho, meta, para) variations.

The term "effective amount" as used herein means a nontoxic but sufficient amount of a compound to provide the desired effect. The exact amount required will vary from patient to patient, depending on the species, age, and general condition of the patient, the severity of the condition being treated, and the particular compound and its mode of administration. Thus, it is not possible to specify an exact "effective amount." However, an appropriate effective amount may be determined by one of ordinary skill in the art using only routine experimentation.

The term "pharmaceutically acceptable" as used herein means a material which is not biologically or otherwise undesirable, i.e., the material may be administered to a patient along with the selected compound without causing any undesirable biological effects or interacting in a deleterious manner with any of the other components of the pharmaceutical composition in which it is contained.

The present invention comprises the design, synthesis and development of a new class of chemotherapeutic agents for the treatment of hormone-responsive disorders. In the new class of chemotherapeutic agents, two components—a message subunit or pharmacophore, present in the nonsteroidal antagonists (e.g., antiandrogens, antiestrogens) and the address subunit found in the steroidal agonists (e.g., androgens, estrogens)—are combined into a single composite entity. In particular, specific compounds in this new class of chemotherapeutic agents target the estrogen and/or the androgen receptors. The general formula for the agents of the invention was determined based on the discovery that the interaction between androgen/estrogen with the receptor involves a two step process. There is an initial association of the hormone (address component) with a specific part of the receptor, called the hormone binding domain, followed by the induction of a conformational change in the receptor (message component) that generates the observed biological response.

Accordingly, the present invention incorporates the "address-message" concept to generate, for example, prostate cancer tissue affinity, selectivity, and efficacy, and employs transition metal catalysts/reagents to prepare the novel therapeutic compounds. As an embodiment, the present invention uses modified palladium catalysts for carbon-carbon (Stille, Suzuki reactions) and carbon-nitrogen/oxygen (Buchwald, Hartwig) coupling reactions. As another embodiment of the present invention, the use of 1D/2D-NMR (Nuclear Magnetic Resonance) and the molecular modeling in the evaluation of the conformational analysis of the target compounds provides the capability for biological and structural data.

The novel therapeutic compounds constitute a structurally unique class of steroidal derivatives, e.g., derivatives of, for example, 17α-(substituted)phenylvinyl-17β-estradiols as estrogens and antiestrogens, and corresponding (nor)testosterones and dihydro-derivatives. In particular, identification of the most potent and selective antagonists for prophylaxis and treatment provides for a more effective treatment of hormone-responsive disorders and thereby prolong the disease-free interval. The present invention provides for a more potent and effective agent which increases the initial response coupled with a slower progression to hormone independence. Additionally, the therapeutic compound of the present invention targets specifically and more selectively thereby reducing the incidence and/or severity of the side effects of anti-estrogen or anti-androgen therapy.

EXAMPLES

The following examples are presented to illustrate the advantages of the present invention and to assist one of ordinary skill in making and using the same. These examples are not intended in any way otherwise to limit the scope of the disclosure.

Preferred antiestrogens/antiandrogens for the prevention or treatment of its corresponding hormone-related disorder acting to inhibit estrogen/androgen action may be prepared accordingly as follows:

Example I

Synthesis and Evaluation of Steroidal Antiestrogens at the 17α-Position of Estradiol Solid Phase Synthesis of 17α-substitued Phenylvinyl Estradiols:

Materials

Reagents and solvents were obtained from commercial sources (Aldrich and Sigma) and were used without further purification. Wang resins and carboxylated polystyrene resins were obtained from Novabiochem. The loading capacities of the resins, 0.75 mmol g$^{-1}$ for the Wang resin and 2.47 mmol g$^{-1}$ for the polystyrene resin, were determined by the manufacturer.

General Methods

A specially designed flask which had a glass frit, through which the reaction mixture could be filtered by applying pressure, was used for the solid phase synthesis. Purifications for the intermediates were done by rinsing resins three times with the following solvents: $CH_2Cl_2$, THF, DMF, MeOH, $CH_2Cl_2$. The cleaved products were purified on a silica gel column chromatography using the appropriate solvents and were characterized by melting point, NMR, IR and electrical analysis. Melting points were determined in open capillary on an Electrothermal Melting Point Apparatus and were uncorrected. IR spectra were recorded on a Perkin-Elmer Model 1600 FT-IR spectrometer. $^1$H and $^{13}$C NMR spectra were obtained with a Varian XL-300 NMR spectrometer at 300 MHz in $CDCl_3$, acetone-$d_6$, or DMSO-$d_6$ as a solvent. Elemental analyses were performed by Atlantic Microlab, Inc. (Norcross, Ga.). As on-resin reaction monitoring methods, color tests and FT-IR methods were used. Bomoscresol green (0.5% in ethanol, pH=8) was used to assay for free carboxylic acids.[18] The color of the stock solution was dark blue and changed to yellow in the presence of free carboxy groups. Antimony (III) chloride solution (25% in $CCl_4$) was also used to determine whether the steroid (17α-ethynyl estradiol) was coupled to the resin and a positive test result for the presence of estradiol was indicated by the color purple (Carr, 1926; Blatz, 1972; Jork, 1990). In addition, a spectro-scopic method (FT-IR) was facilitated to detect chromophore change by reaction.

Preparation of the Carboxylated Resin (Method A). The Wang resins (1 g, 0.75 mmol) were swelled in the $CH_2Cl_2$ overnight and rinsed twice with THF, $CH_3OH$, $CH_2Cl_2$ and acetone. Acetone (5 mL) was added to the swelled resins. To the slurry was added 1 mL of Jones reagent (Bowden, 1946) in a dropwise manner. The mixture was allowed to stand at room temperature for 24 h. The resin mixture was rinsed twice with water-acetone (1:1), $CH_3OH$, DMF, DMSO and $CH_2Cl_2$ and dried in vacuo. The loading capacity after the carboxylation reaction was 0.4–0.6 mmol g$^{-1}$, which was determined with the coupling of 17α-ethynyl estradiol to the resin. The aliquot of the resins was characterized by FT-IR. FT-IR (KBr) v: 3000–3500 (OH, broad), 1690 (C=O, broad), 1603, 1492, 1452 (aromatic ring), 1279 (C—O).

(Method B). The carboxylation of a polystyrene resin was accomplished using the method described by Farrall et al. (Farrall, 1976). FT-IR (KBr) v: 3420 (OH, broad), 1630 (C=O, broad), 1200–1400 (C—O, broad). Loading capacity: 1.5–1.9 mmol g$^{-1}$.

Coupling 17α-ethynyl Estradiol to the Resins

The carboxylated Wang resin (2.3 g) or polystyrene resin (2.5 g) was placed in the reactor equipped with a magnetic stirrer. The resin was swelled in the ch$_2$cl$_2$ for 5 h and washed sequentially with THF, DMF, CH$_3$OH, THF and CH$_2$CL$_2$. To the resin was added 0.23 g (1.1 mmol) of dicyclohexylcarbodiimide (DDC) and 5 ml of CH$_2$CL$_2$ and the mixture was mildly stirred for 10 min. To the slurry was added 0.75 g (2.6 mmol) of 17α-ethynyl estradiol dissolved in 10 ml of CH$_2$CL$_2$-DMF (9:1) solvent and catalytic amount of 4-dimethylaminopyridine (DMAP). The reaction mixture was stirred for 5 min and then allowed to stand at room temperature for 24 h. The resin was washed three times with CH$_2$CL$_2$ CH$_3$OH, IPA (60° C.), THF and DMF (60° C.) (Morales, 1998). The rinsed resin was dried under vacuum for 5 h. The actual loading of the resin was determined by quantitative measurement of the material by cleavage from known weight of resin using 5 N-NaOH in CH$_3$OH-dioxane (1:3). The resin-bound steroids were characterized by FT-IR and the cleaved compounds by $^1$H and $^{13}$C NMR before proceeding to the next step. The loading capacity of each resin was shown in Method A and B; FT-IR (KBr) v; 3437 (17β—OH), 3301 (17α-C≡C-H), 1735 (C=O), 1607, 1493, 1452 (aromatic ring), 1216(C—O).

Hydrostannylation (Method A). The 17α-ethynyl estradiol coupled to the resin (0.49 g, 0.57 mmol g$^{-1}$) was placed in a dry 25 mL reaction flask equipped with a reflux condenser and a magnetic stirrer and was swelled in THF for 1 h. To the slurry in the dry THF were treated triethylborane (0.7 mL) and tributyltin hydride (1 mL) (Nozaki, 1989). The mixture was allowed to stand at 60–70° C. for 48 h under a nitrogen atmosphere. The reaction mixture was washed three times each with CH$_2$Cl$_2$, CH$_3$OH, DMF, CH$_2$Cl$_2$ and ethyl acetate and the resultant resin was dried in vacuo. An aliquot of the resins was cleaved with 5 N NaOH in CH$_3$OH—CH$_2$Cl$_2$ (1:2) to afford a mixture of E- and Z-isomers. The mixture was separated by chromatography on the silica gel to give a 23% (0.13 mmol g$^{-1}$) yield of products, consisting of 21% (0.12 mmol g$^{-1}$) of the E-isomer and 2% (0.01 mmol g$^{-1}$) of the Z-isomer. R$_f$ (Z-isomer=0.58 (hexane-ethyl acetate, 4:1); Rf (E-isomer)=0.44 (hexane-ethyl acetate, 4:1); Amorphous; $^1$H NMR (CDCl$_3$, 300 MHz, δ), 0.88 (s, 3H, C$_{18}$-methyl-H), 1.2–2.4 (m, steroid envelope and tributyl-stannyl-H), 2.7–2.9 (m, 2H, C$_6$—H), 6.06 (d, 1H, J=19.4 Hz, C$_{21}$ vinyl-H), 6.22 (d, 1H, J=19.4 Hz, C$_{20}$ vinyl-H), 6.79(d, 1H, J=2.4 Hz, C$_4$—H), 6.84 (dd, 1H, J=2.6, 8.4 Hz, C$_2$—H), 7.28 (d, 1H, J=8.8 Hz, C$_1$—H); $^{13}$C NMR (CDCl$_3$), 9.6 (C$_{22}$, 4C), 13.7 (C$_{24}$, 4C), 14.2 (C$_{18}$), 23.4 (C$_{15}$), 26.4 (C$_{11}$), 27.3 (C$_{25}$, 4C), 27.4 (C$_7$), 29.2 (C$_{23}$, 4C), 29.6 (C$_6$), 32.4 (C$_{12}$), 35.9 (C$_{16}$), 39.4 (C$_8$), 43.8 (C$_9$), 46.7 (C$_{13}$), 49.0(C$_{14}$), 85.6 (C$_{17}$), 112.6 (C$_2$), 115.2 (C$_4$), 124.6 (C$_{21}$), 126.5 (C$_1$), 132.7 (C$_{10}$), 138.3 (C$_5$), 152.4 (C$_{20}$), 153.3 (C$_3$), FT-IR (KBr) v: 3445 (17β-OH, broad, 1719 (C=O), 1653 (C=C), 1607, 1493, 1451 (aromatic ring), 1217 (C—O).

(Method B). The 17α-ethynyl estradiol (3 g, 10 mmol) was dissolved in THF and treated with triethylborane (2 mL, 17 mmol) and tributyltin hydride (3 g, 11 mmol). The mixture was stirred with a magnetic stirrer at 60° C. for 16 h. The crude mixture (7.73 g) was evaporated to dryness, redissolved in the CH$_2$Cl$_2$, and transferred to the swelled resin (5 g) in CH$_2$Cl$_2$ in the presence of DCC. A catalytic amount of DMAP was added to the mixture, which was allowed to stand for 24 h. The resultant functionalized resin was treated as previously described. The total loading for both E- and Z-isomers was 0.59 mmol g–1 with 0.56 mmol g$^{-1}$ of E-isomer and 0.03 mmol g$^{-1}$ of Z-isomer, however, by the dry weight difference between pre- and post-reaction, the loading for both E- and Z-isomers was 1.55 mmol g$^{-1}$.

Electrophilic Destannylation on the Resin

The Stille reaction was used to couple the anchored E- and Z-stannylvinyl estradiol to aryl halides. The resin was added to the reaction flask, swelled in the CH$_2$Cl$_2$, subsequently treated with 10 mL of anhydrous toulene. To the resultant slurry was added a 3–4 fold excess of the functionalized aryl halide, 1–2 crystals of 3.5-di-t-butyl-4-hydroxytoulene (BHT), and Pd(PPh$_3$) 4 (Bowden, 1946; Farrall, 1976). The reaction was allowed to proceed at 90–100° C. for 24 h. After cooling, the resin was washed as previously described, dried in vacuo and weighed.

Cleavage

The resin was swelled in CH$_2$Cl$_2$ (10 mL) containing 3 mL of 5 N-NaOH in CH$_3$OH-Dioxane (1:3) and stirred for 1 h. This cleavage step was repeated three times. Most of the product was collected from the first attempt, a small amount by second hydrolysis, and almost none from the third trial. The fractions were combined, evaporated to dryness, and partitioned between ethyl acetate and water. Acetic acid (1 mL, 5%) was added. The organic phase was washed with 10% aqueous NaHCO$_3$ to remove the residual acetic acid, dried over MgSO$_4$, filtered and evaporated to dryness. The crude product was purified by silica gel column chromatography or by recrystallization from the appropriate solvent.

17α-20E-21-(2-Trifluoromethylphenyl)-19-norpregna-1,3,5 (10),20-tetraene-3,17β-diol (17α-E-(2-trifluoromethylphenyl)-vinyl estradiol) (4a). Yield=38%; R$_f$=0.19 (hexane-ethyl acetate, 4:1); mp 224–225° C.; $^1$H NMR (300 MHz, Acetone-d$_6$, 6) 1.02 (s, 3H, C$_{18}$ methyl-H), 1.2–2.4 (m, steroid envelope), 2.7–2.9 (m, 2H, C$_6$—H), 3.98(s, 1H, 17P hydroxyl-H), 6.53 (d, 1H, J=2.3 Hz, C$_4$—H), 6.58 (dd, 1H, J=2.6, 8.5 Hz, C$_2$—H), 6.64 (d, 1H, J=15.7 Hz, C$_{20}$ vinyl-H), 7.0 (dd, 1H, J=2.5, 15.8 Hz, C$_{21}$ vinyl-H), 7.07 (d, 1H, J=8.7 Hz, C$_1$—H), 7.42 (t, 1H, J=7.8 Hz, C$_{26}$—H), 7.60 (t, 1H, J=7.3 Hz, C$_{25}$—H), 7.69 (d, 1H, J=7.8 Hz, C$_{27}$—H), 7.81 (d, 1H, J=8.3 Hz, C$_{24}$—H), 7.98 (s, C$_3$ hydroxy-H); $^{13}$C NMR (75.4 MHz, Acetone-d$_6$, 8) 14.7 (C$_{18}$), 24.1 (C$_{15}$) 27.2 (C$_{11}$), 28.3 (C$_7$), (C$_6$), 33.4 (C$_{12}$), 37.5 (C$_{16}$), 40.7 (C$_8$); 44.6 (C$_9$), 48.4 (C$_{13}$), 50.0 (C$_{14}$), 84. 3 (C$_{17}$), 113.5 (C$_2$), 115.9 (C$_4$), 123.4 (C$_{21}$), 125.6 (q, J=273.2 Hz, C$_{28}$:CF$_3$), 126.4 (q, J=5.8 Hz, C$_{24}$), 127.0 (C$_1$), 127.4 (q, J=29.4 Hz, C$_{23}$), 127.8 (C$_{26}$), 128.6 (C$_{27}$), 132.0 (C$_{25}$), 133.2 (C$_{10}$), 137.9 (C$_{22}$), 139.1 (C$_5$), 142.4 (C$_{20}$), 155.9 (C$_3$); Anal. Calcd for C$_{27}$H$_{29}$O$_2$F$_3$: C, 73.30; H, 6.56. Found: C, 73.04; H, 6.68.

17α-20E-21-(3-Trifluoromethylphenyl)-19-norpregna-1,3,5 (10),20-tetraene-3,17β-diol (17α-E-(3-trifluoro methylphenyl)-vinyl estradiol) (5a). Yield=33%; R$_f$ (E-isomer)=0.19 (hexane-ethyl acetate, 4:1); mp 244–246° C.; $^1$H NMR (300

MHz, Acetone-$d_6$, 6), 1.01 (s, 3H, $C_{18}$-methyl), 1.2–2.4 (m, steroid envelope), 2.7–2.9 (m, 2H, $C_6$—H), 3.98 (s, 1H, 17β hydroxyl-H), 6.53 (d, 1H, J=2.6 Hz, $C_4$—H), 6.58 (dd, 1H, J=2.6, 8.3 Hz, $C_2$—H), 6.74 (d, 1H, J=16 Hz, $C_{21}$ vinyl-H), 6.84 (d, 1H, J=16 Hz, $C_{20}$ vinyl-H), 7.06 (d, 1H, J=8.3 Hz, $C_1$—H), 7.54–7.56 (m, 2H, $C_{25}$, $C_{27}$—H), 7.75–7.79 (m, 2H, $C_{23}$, $C_{26}$—H), 7.93 (s, $C_3$-hydroxy-H); $^{13}$C NMR (75.4 MHz, Acetone-$d_6$, δ), 14.7 ($C_{18}$), 24.1 ($C_{15}$), 27.3 ($C_{11}$), 28.3 ($C_7$), ($C_6$), 33.5 ($C_{12}$), 37.5 ($C_{16}$), 40.7 ($C_8$), 44.6 ($C_9$), 48.4 ($C_{13}$), 50.1 ($C_{14}$), 84.2 ($C_{17}$), 113.5 ($C_2$), 115.9 ($C_4$), 123.6 (q, J=5.6 Hz, $C_{25}$), 124.1 (q, J=3.7 Hz, $C_{23}$), 125.4 (q, J=271 Hz, $C_{28}$:$CF_3$), 126.0 ($C_{26}$), 127.0 ($C_1$), 130.2 ($C_{21}$), 130.7 ($C_{27}$), 131.2 (q, J=32 Hz, $C_{24}$), 132.0 ($C_{10}$), 138.4 ($C_5$), 139.7 ($C_{20}$), 139.9 ($C_{22}$), 155.9 ($C_3$);

Anal. Calcd for $C_{27}H_{29}O_2F_3$: C, 73.30; H, 6.56. Found: C, 73.42; H, 6.68.

17α-20E-21-(4-Trifluoromethylphenyl)-19-norpregna-1,3,5 (10),20-tetraene-3, 17β-diol (17α-E-(4-trifluoro methylphenyl)-vinyl estradiol) (6a). Yield=49%; $R_f$=0.15 (hexane-ethyl acetate, 4:1); mp 215–217° C.; $^1$H NMR (Acetone-$d_6$, 300 MHz, 8), 1.02 (s, 3H, $C_{18}$ methyl-H), 1.2–2.4 (m, steroid envelope), 2.7–2.9 (m, 2H, $C_6$—H), 3.90 (s, 1H, 17β hydroxyl-H), 6.53 (d, 1H, J=2.6 Hz, $C_4$—H), 6.58 (dd, 1H, J=2.6, 8.4 Hz, $C_2$—H), 6.73 (d, 1H, J=16 Hz, $C_{21}$ vinyl-H), 6.85 (d, 1H, J=16 Hz, $C_{20}$ vinyl-H, 7.07 (d, 1H, J=8.3 Hz, $C_1$—H), 7.64 (d, 2H, J=8.7 Hz, $C_{23}$, $C_{27}$—H), 7.70 (d, 2H, J=8.6 Hz, $C_{24}$, $C_{26}$—H), 8.0 (s, $C_3$-hydroxy-H); $^{13}$C NMR (75.4 MHz, Acetone-$d_6$, 6) 14.7 ($C_{18}$), 24.1 ($C_{15}$), 27.3 ($C_{11}$), 28.3 ($C_7$), ($C_6$), 33.5 ($Cl_2$), 37.6 ($C_{16}$), 40.7 ($C_8$), 44.6 ($C_9$), 48.5 ($C_{13}$), 50.2 ($Cl_4$), 84.2 ($C_{17}$), 113.5 ($C_2$), 115.9 ($C_4$), 125.4 (q, J=270.6 Hz, $C_{28}$:$CF_3$), 126.0 ($C_{21}$), 126.2 (q, J=3.5 Hz, $C_{26}$), 126.2 (q, J=3.5 Hz, $C_{24}$), 127.0 ($C_1$), 127.6 ($C_{23}$, $C_{27}$), 128.9 (q, J=32 Hz, $C_{25}$), 132.0 ($C_{10}$), 138.4 ($C_5$), 140.6 ($C_{20}$), 142.7 ($C_{22}$), 155.9 (C3);

Anal. Calcd for $C_{27}H_{29}O_2F_3$: C, 73.30; H, 6.56. Found: C, 73.36; H, 6.79.

17α-20Z-21-(4-Trifluoromethylphenyl)-19-norpregna-1,3,5 (10),20-tetraene-3,17α-diol (17α-Z-(4-trifluoro methylphenyl)-vinyl estradiol) (6b). Yield=17%; $R_f$=0.29 (hexane-ethyl acetate, 4:1); $^1$H NMR (300 MHz, Acetone-$d_6$, 6) 0.97 (s, 3H, $C_{18}$ methyl-H), 1.2–2.4 (m, steroid envelope), 2.7–2.9 (m, 2H, $C_6$—H), 3.89 (s, 1H, 17β hydroxyl-H), 6.12 (d, 1H, J=12.9 Hz, $C_{21}$ vinyl-H), 6.48–6.62 (m, 3H, $C_2$, $C_4$, $C_{20}$ vinyl-H), 7.11 (d, 1H, J=8.1 Hz, $C_1$—H), 7.59 (d, 2H, J=8.4 Hz, $C_{23}$, $C_{27}$—H), 7.80 (d, 2H, J=8.4 Hz, $C_{24}$, $C_{26}$—H), 7.95 (s, $C_3$ hydroxy-H).

17α-20E-21-(2-Methylphenyl)-19-norpregna-1,3,5(10), 20-tetraene-3, 17β-diol (17α-E-(2-methylphenyl)-vinyl estradiol) (7a). Yield=38%; $R_f$=0.18 (hexane-acetone, 4:1); mp 199–200° C.; $^1$H NMR (Acetone-$d_6$, 300 MHz, δ), 1.01 (s, 3H, $C_{18}$ methyl-H), 1.2–2.4 (steroid envelope), 2.34 (s, 3H, $C_{28}$ methyl-H), 2.7–2.9 (m, 2H, $C_6$—H), 3.84 (s, 1H, 17β hydroxyl-H), 6.44 (d, 1H, J=16 Hz, $C_{21}$ vinyl-H), 6.52–6.63 (m, 2H, $C_2$, $C_4$—H), 6.83 (d, 1H, J=16 Hz, $C_{20}$ vinyl-H), 7.07 (d, 1H, J=8.3 Hz, $C_1$—H), 7.10–7.15 (m, 3H, $C_{24}$, $C_{25}$, $C_{26}$—H), 7.48 (d, 1H, J=6.8 Hz, $C_{27}$—H), 7.97 (s, $C_3$ hydroxy-H); $^{13}$C NMR (75.4 MHz, Acetone-$d_6$, δ) 14.7 ($C_{18}$), 19.9 ($C_{28}$, methyl), 24.1 ($C_{15}$), 27.3 ($C_{11}$), 28.3 ($C_7$), ($C_6$), 33.5 ($C_{12}$), 37.5 ($C_{16}$), 40.7 ($C_8$), 44.7 (Cg), 48.2 ($C_{13}$), 50.1 ($C_{14}$), 84.2 ($C_{17}$), 113.5 ($C_2$), 115.9 ($C_4$), 125.4 ($C_{26}$), 126.5 ($C_{25}$), 126.9 ($C_{24}$), 127.0 ($C_1$), 127.7 ($C_{21}$), 130.8 ($C_{27}$), 132.0 ($C_{10}$), 135.9 ($C_{20}$), 137.9 ($C_{22}$), 138.4 ($C_5$), 138.8 ($C_{23}$), 155.9 ($C_3$); Anal. Calcd for $C_{27}H_{32}O_2$: C, 83.51; H, 8.25. Found: C, 83.79; H, 8.65.

17α-20E-21-(3-Methylphenyl)-19-nonpregna-1,3,5(10), 20-tetraene-3, 17β-diol (17α-E-(3-methylphenyl)-vinyl estradiol) (8a). Yield=75%; $R_f$=0.17 (hexane-acetone, 4:1); mp 204–205° C.; $^1$H NMR (300 MHz, Acetone-$d_6$, 6), 1.00 (s, 3H, $C_{18}$ methyl-H), 1.2–2.4 (m, steroid envelope), 2.31 (s, 3H, $C_{28}$ methyl-H), 2.7–2.9 (m, 2H, $C_6$—H), 3.74 (s, 1H, 17β hydroxyl-H), 6.52–6.63 (m, 4H, $C_4$, $C_2$, $C_{21}$ vinyl, $C_{20}$ vinyl-H), 7.03 (d, 1H, J=7.3 Hz, $C_{25}$—H)., 7.07 (d, 1H, J=8.7 Hz, $C_1$—H), 7.16–7.31 (m, 3H, J=7.4 Hz, $C_{23}$, $C_{26}$, $C_{27}$—H), 7.93 (s, 1H, $C_3$ hydroxy-H); $^{13}$C NMR (75.4 MHz, Acetone-$d_6$, 6) 14.8 ($C_{18}$), 21.4 ($C_{28}$; methyl), 24.1 ($C_{15}$), 27.3 ($C_{11}$), 28.4 ($C_7$), ($C_6$), 33.5 ($C_{12}$), 37.4 ($C_{16}$), 40.8 ($C_8$), 44.7 (Cg), 48.3 ($C_{13}$), 50.2 ($C_{14}$), 84.2 ($C_{17}$), 113.6 ($C_2$), 116.0 ($C_4$), 124.4 ($C_{27}$), 127.0 (Cl), 127.7 ($C_{25}$), 127.8 ($C_{26}$), 128.5 ($C_{21}$), 129.2 ($C_{23}$), 132.2 ($C_{10}$), 137.0 ($C_{20}$), 138.4 ($C_5$), 138.7 ($C_{22}$, $C_{24}$), 155.9 ($C_3$); Anal. Calcd for $C_{27}H_{32}O_2$: C, 83.51; H, 8.25. Found: C, 83.23; H, 8.42.

17α-20Z-21-(3-Methylphenyl)-19-norpregna-1,3,5(10), 20-tetraene-3, 17β-diol (17α-Z-(3-methylphenyl)-vinyl estradiol) (8b). Yield=54% (0.01 g); $R_f$=0.25 (hexane-acetone, 4:1); $^1$H NMR (300 MHz, Acetone-$d_6$, δ) 0.95 (s, 3H, $C_{18}$ methyl-H), 1.2–2.4 (m, steroid envelope), 2.31 (s, 3H, $C_{28}$ methyl-H), 2.7–2.9 (m, 2H, $C_6$—H), 3.27 (s, 1H, 17β hydroxyl-H), 5.96 (d, 1H, J=13.1 Hz, $C_{21}$ vinyl-H, 6.44 (d, 1H, J=13.1 Hz, $C_{20}$ vinyl-H), 6.53 (d, 1H, J=2.6 Hz $C_4$—H), 6.60 (dd, 1H, J=2.6, 8.3 Hz, $C_2$—H), 7.03 (d, 1H, J=7.3 Hz, $C_{25}$—H), 7.11 (d, 1H, J=8.3 Hz, $C_1$—H), 7.17 (t, 1H, J=7.6 Hz, $C_{26}$—H), 7.38–7.43 (m, 2H, $C_{23}$, $C_{27}$—H), 7.95 (s, 1H, $C_3$ hydroxy-H); $^{13}$C NMR (75.4 MHz, Acetone-$d_6$, 6) 14.58 ($C_{18}$), 21.42 ($C_{28}$: methyl). 23.85 ($C_{15}$), 27.40 ($C_{11}$), 28.30 ($C_7$), ($C_6$), 32.97 ($Cl_2$), 38.4 ($C_{16}$), 40.9 ($C_8$), 44.7 (Cg), 48.8 ($C_{13}$), 50.1 ($C_{14}$), 84.3 ($C_{17}$), 113.6 ($C_2$), 116.0 ($C_4$), 127.1 ($C_1$), 127.8 ($C_{27}$), 128.1 (C25), 128.3 ($C_{26}$), 129.7 ($C_{21}$), 131.4 ($C_{23}$), 132.0 ($C_{10}$), 137.1 ($C_{20}$), 137.6 ($C_{24}$), 138.45 ($C_5$), 138.5 ($C_{22}$), 155.9 ($C_3$); Anal. Calcd for $C_{29}H_{36}O_3$: C, 80.55; H, 8.33. Found: C, 80.00; H, 8.41

17α-20E-21(4-Methoxyphenyl)-19-norpregna-1,3,5,(10), 20-tetraene-3, 17β-diol (17α-E-(4-methoxyphenyl)-vinyl estradiol) (9a). Yield=36%; $R_f$=0.23 ($CHCl_3$—$CH_3OH$, 99:1); $^1$H NMR (300 MHz, Acetone-$d_6$, δ) 0.99 (s, 3H, $C_{18}$ methyl-H), 3.68 (s, 1H, 17β hydroxy-H), 3.78 (s, 3H, $C_{28}$:methoxy-H), 6.46 (d, 1H, J=16.1 Hz, $C_{21}$—H), 6.51–6.59 (m, 3H, $C_2$, $C_4$, $C_{20}$—H), 6.88 (d, 2H, J=8.8 Hz, $C_{24}$, $C_{26}$—H); 7.07 (d, 1H, J=8.3 Hz, Cl-H); 7.39 (d, 2H, J=8.8 Hz, $C_{23}$, $C_{27}$—H), 7.95 (s, 1H, $C_3$ hydroxy-H); $^{13}$C NMR (75.4 MHz, Acetone-$d_6$, δ) 14.7 ($C_{18}$), 24.1 ($C_{15}$), 27.3 ($C_{11}$), 28.3 ($C_7$), ($C_6$), 33.4 ($C_{12}$), 37.3 ($C_{16}$), 40.7 ($C_8$), 44.7 (Cg), 48.2 ($C_{13}$), 50.0 ($C_{14}$), 55.5 ($C_{28}$:methoxy), 84.1 ($C_{17}$), 113.5 ($C_2$), 114.7 ($C_{24}$, $C_{26}$), 115.9 ($C_4$), 127.0 ($C_1$), 127.0 ($C_{21}$), 128.3 ($C_{23}$, $C_{27}$), 131.4 ($C_{22}$), 132.1 (C10), 134.9 ($C_{20}$), 138.4 ($C_5$), 155.9 ($C_3$), 159.9 ($C_{25}$).

In the above procedures, the Solid Phase Synthesis methodology was applied using carboxylated resins to generate a series of novel ER-LBD ligands, or estradiol derivatives. The purification steps were simplified and simultaneously produced both the E- and Z-isomers. Yield may be improved by modifications in both the coupling and cleavage steps for a chemically more sensitive Z-isomer.

One of the key elements of the synthetic scheme was the selection of a linker that could be both formed and cleaved under mild conditions. 17α-substituted estradiols were unstable under strongly acidic conditions such as those frequently used to release products from the resins. Therefore the resin of choice was carboxylated polystyrene which could be esterified under neutral conditions and ultimately cleaved with mild base. Compound 8a was prepared using the carboxylated resin obtained either by oxidation of a Wang resin using Jones reagent (Bowden, 1946) or by carboxylation of a polystyrene resin via lithiation with n-butyl lithium (Farrall, 1976). The reactions for both methods were easily monitored by the appearance of the 1700 cm$^{-1}$ absorption in the FT-IR spectrum. The loading capacity of the carboxylated resins was determined by coupling 17α-ethynyl estradiol onto the resins using DCC in the presence of catalytic amount of DMAP and measuring its subsequently cleaved estradiol derivatives from the aliquot of the resins. The loading$^1$ of oxidized Wang resin was 0.4–0.6 mmol g$^{-1}$ and that of carboxylated polystyrene was 1.5–1.9 mmol g$^{-1}$. Once the utility of coupling through the ester linkage using carboxy polystyrene resin was confirmed, the commercially available carboxy poolystyrene was used for the remainder of the work. The loading yield of the reaction using the resins with already known loading capacity (2.47 mmol g$^{-1}$) was 82%. The yield was determined by 'cleave and characterize' methods.

Figure 1:
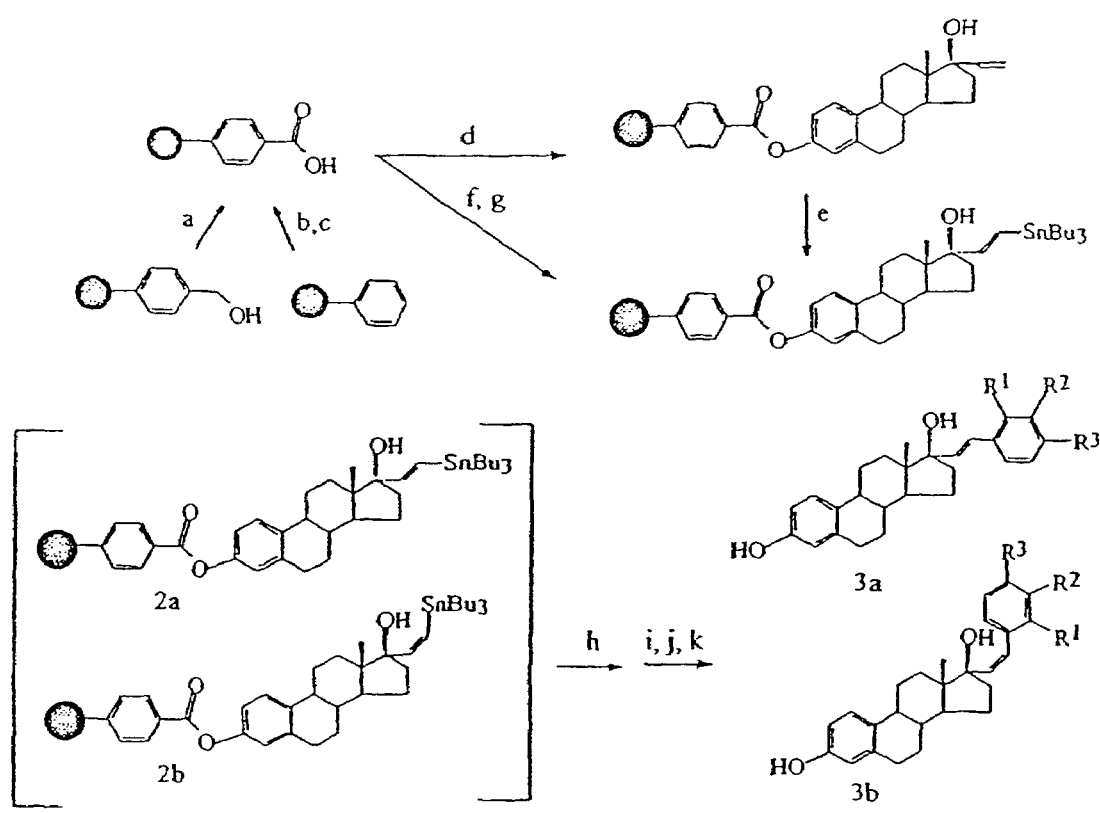
FIG. 1 depicts the synthesis of the estradiol analogs according to the invention by coupling the 3-phenolic group of 17α-ethynyl estradiol to the carboxy polystyrene resin. The reagents and conditions used were as follows.

As shown in FIG. 1, the synthesis of the analogs was initiated by coupling the 3-phenolic group of 17α-ethynyl estradiol to the carboxy polystyrene resin. The steroids on the resins were confirmed by an antimony (III) chloride assay (Carr, 1926; Blatz, 1972; Jork, 1990). Due to the absence of color change with bromocresol green, no free carboxylic acid groups remained on the resin (Gordon, 1972). The appearance of a peak at 3301 cm$^{-1}$ in the IR spectrum, corresponding to the C—H stretch of the ethynyl group, also confirmed that the reaction and a shift of carbonyl absorption to higher frequency (from 1690–1734 cm$^{-1}$) was also observed.

The subsequent hydrostannylation step incorporated either the use of hydrostannylation of bound ethynyl estradiol (Method A) or hydrostannylation of ethynyl estradiol in solution phase synthesis followed by coupling to the resin (Method B). The resin-bound 17α-ethynyl estradiol was hydrostannylated with tributyltin hydride using triethylborane as a radical initiator (Nozaki, 1989) to afford a mixture of the 17α-E/Z-tri-n-butylstannylvinyl estradiol in 20–30% (0.12 mmol g$^{-1}$ of E, 0.01 mmol g-1 of Z) loading yields. Varying the reaction conditons, e.g. different solvents, temperatures, or reaction times, did not improve the yields. Therefore, a direct coupling of 17α-E/Z-tri-n-butylstannyl-vinyl estradiols was used to overcome the low efficiency of this step. 17α-Ethynyl estradiol was hydrostannylated to 60° C. and the crude mixture was directly transferred to the resin slurry in CH$_2$Cl$_2$. The mixture was treated with a 2–3 fold excess of DCC and a catalytic amount of DMAP was added. The loading yield for the coupling reaction was 0.59 mmol g$^{-1}$ with a Z/E ratio=1:20. The low loading yield was due to the use of the acetic acid for the protonation of phenoxide ion after cleavage, subjecting the products to protiodestannylation and reducing the expected loading yield. Because the cleavage after hydrostannylation did not provide a precise loading yield, the dry weight difference between pre-and post-reaction was subsequently used to determine the loading yield. Using the dry weight difference method, the yield for the hydrostannylation reaction was 1.55 mmol g$^{-1}$ for both E- and Z-isomers. Because hydrostannylation on the resin did not afford satisfactory yields. Method B was the method of choice. The ratio of E and Z isomers is a function of the reaction temperature, time and stoichiometric ratio of tributyltin hydride to alkyne. At 60° C. the reaction generated greater than 20:1 (E/Z) ratio bound to the solid phase. To increase the ratio of the Z-isomer, triethylborane was used as a radical initiator and the reaction was run at low temperature. The proportion of the Z-isomer (Z/E=1:10) was increased. However, the reaction required a longer time and the loading yield for the hydrostannylation was slightly lower than at higher temperature (1.44 mmol g$^{-1}$ by the dry weight difference method) because of more unreacted 17α-ethynyl estradiol in the reaction mixture.

The resin-bound hydrostannnylated estradiol was subjected to the Stille coupling reaction (Stille, 1985) using a variety of substituted aryl halides to generate the target compounds (see Table 2). As shown in FIG. 1, Pd(PPh$_3$)$_4$ was used as the catalyst for the reaction and 3,5-di-t-butyl-4-hydroxytoluene (BHT) was added as a scavenger. The use of Pd(PPh$_3$)$_4$ generated an insoluble by-product that caused coloration of the resin, however, it was easily removed by rinsing it through the built-in filter (50–70 μm). After completion of all the reaction steps, the product was cleaved from the resin by saponification with 5 N NaOH dissolved in CH$_3$OH-Dioxane (1:3).

TABLE 2

| Compound | R$^1$ (ortho) | R$^2$ (meta) | R$^3$ (para) | Yield (%) |
|---|---|---|---|---|
| 4a:E | CF$_3$ | H | H | 38 |
| 5a:E | H | CF$_3$ | H | 33 |
| 6a:E | H | H | CF$_3$ | 49 |
| 6b:Z | H | H | CF$_3$ | 17 |
| 7a:E | CH$_3$ | H | H | 38 |
| 8a:E | H | CH$_3$ | H | 75 |
| 8b:Z | H | CH$_3$ | H | 54 |
| 9a:E | H | H | OCH$_3$ | 36 |

As shown in Table 2, the unoptimized yields of the Stille reactions on solid phase ranged from 17–75%, comparable to those observed for solution phase synthesis. Compounds 5a (para-trifluoromethylphenyl, E-isomer) and 5b (para-trifluoromethylphenyl, Z-isomer) were isolated from the Stille reaction in a ratio of 98:2. Compound 7a (meta-methylphenyl, E-isomer) and 7b (meta-methylphenyl, Z-isomer) were also obtained in a ratio of 96:4. Although the Z-tri-n-butylstannyl vinyl estradiol was initially present on the resin, no Z-isomers of compounds 3a, 4a, 6a, or 8a were isolated from the Stille coupling, instead, 17α-vinyl estradiol, resulting from protiodestannylation was recovered as a side product. Because an excess of reagent was used to drive the reaction to completion, unreacted hydrostannylated 17α-E/Z-(tri-n-butylstannyl)-vinyl estradiol was no detected after the Stille reaction. It is possible that the Z-isomers either isomerized to thermodynamically more stable E-isomers under the conditions required for the Stille reaction or underwent protiodestannylation. As previously observed, the Z-isomer is much more susceptible to protiodestannylation than the E-isomer and the appearance of the side product under either solid phase or solution phase synthesis was approximately the same.

The isolated product were characterized by standard spectroscopic methods (FT-IR, $^1$H and $^{13}$C NMR) and analytical methods. The data were consistent with the proposed structures. Stereochemical assignments for compounds 5a and 5b were based on the $C_{20}$, $C_{21}$ olefinic proton coupling constants for which E=16 Hz and Z-12.9 Hz, respectively. For compounds 7a and 7b, the observed coupling constants were 18.2 Hz of the $C_{20}$ E-vinyl proton and 13.1 Hz for the $C_{20}$ Z-vinyl proton. In $^{13}$C NMR, long range couplings were observed for the compounds 3a-5a and 5b containing the trifluoromethyl group. Coupling with strongly electronegative fluorine was found at the carbon directly attached to the fluorine ($^1J_{C-F}$) and one ($^2J_{C-F}$) and two carbons distant ($^3J_{C-F}$). The carbons appeared as quartets and the coupling constants were approximately $^1J_{C-F}$=270 Hz. $^2J_{C-F}$=32 Hz. $^3J_{C-F}$=3–5 HZ respectively.

Variability of Ortho, Meta, Para-Substitutions

Ortho, meta, and para (trifluoromethyl)phenylvinyl estradiol isomers were evaluated for estrogen receptor-ligand binding domain (ER-LBD) affinity. The properties of the aryl substituent and its position on the ring (ortho/meta/para) affect receptor binding.

Trifluoromethyl group was introduced onto phenylvinyl estradiol either at the ortho, meta, or para positions. These compounds were examined for their ability to stimulate or inhibit estrogen responses in two assay systems. The initial system evaluated the ability of the ligand to stimulate the proliferation of MCF-7 cells and as the results in FIG. 11 indicate, the ortho-isomer produced a full agonist response comparable to that of estradiol. When the ligand was added to the cells in the presence of 1 nM estradiol, there was neither an enhancement nor a diminution of the proliferative response. The meta- and para-isomers gave substantially different profiles. The meta-isomer demonstrated a weak proliferative effect at doses greater than 1 nM and antagonized the effects of estradiol at the same doses. The para-isomer, however, did not elicit a proliferative response until a 10 nM dose was employed and decreases in the estradiol effects were observed below 1 nM. Therefore, the position of the trifluoromethyl group exerted a significant effect on the efficacy of the ligand.

These trifluoromethyl substituted compounds were also studied with an immature female rat uterotrophic growth assay; the results are shown in FIGS. 12, 13, and 14. In the estrogenic assay, the ortho-isomer produced an effect comparable to estradiol at a 3 nM level and substantial estrogenic effects at 10 and 100 nM. The meta- and para-isomers, however, demonstrated little or no estrogenic effects, even at 10 and 100 nM. Therefore, the agonist responses observed in the in vitro cell proliferation assay were carried over to the intact animal as well. The antiestrogen assay evaluated the ability of the isomers to block the uterotrophic effect induced by 1 nM estradiol. Under these conditions, the ortho isomer produced an enhancement of the estrogenic response at both 10 and 100 nM. The meta-isomer demonstrated no significant effect on the estradiol response at either dose, however, the para isomer reduced the estrogenic response at the 100 nM level. Therefore, in both estrogen responsive cells and tissues these new ligands are producing differential responses in affinity and efficacy related to the site of trifluoromethyl substitution on the phenyl ring.

Example II

Development of Antiandrogens

The cellular target for antiandrogen therapy, the androgen receptor (AR), is a member of the nuclear receptor superfamily which has been studied extensively over the past decade (Tsai, 1994). Members of this receptor bear a strong structural similarity (homology) and utilize similar signaling pathways to express their biological actions. At the molecular level, the AR, like the other steroid hormone receptors, is composed of discrete domains that are responsible for specific functions. The hormone binding domain (HBD), the sequence of aminoacids near the N-terminus of the AR, recognizes and binds testosterone with high affinity but not other hormones or small endogenous molecules (Weatherman, 1999; Simons, 1998). This region of the receptor has been examined using X-ray crystallography to elucidate the aminoacid residues responsible for the recognition of specific hormones. The hormone binding domains on the estrogen receptor (ER), progesterone receptor (PgR) and retinoic acid receptor (RAR) provide a common fold for the endogenous hormone, which also strongly suggest the types of conformational changes that occur upon ligand binding (Brzozowski, 1997; Tannenbaum, 1998; Shiau, 1998; Williams, 1998; Renaud, 1995; Klaholz, 1998). The conformational changes, particularly those associated with helix-12, assist in the recruitment of specific coactivator proteins that appear to initiate the action of the general transcription apparatus (Resche-Rigon, 1998; McKenna, 1999; Klinge, 2000).

In accordance with the present invention, the steroidal nucleus is the address component, which directs the molecule to the HBD where, for agonists, the D-ring substituents direct helix-12 into a conformation that exposes the Activation Function-2 (AF-2) or message component. For known ER and PgR antagonists, the steroid nucleus present in most drugs provides the appropriate address. However, the incorporation of an additional functional group interferes with the movement of helix-12, and produces a full or partial antagonist response (message). Most of the antihormones known in the art incorporate that additional functional group at either the 11β- or 7α-position of the steroid (see FIG. 7). The present invention shows that antagonism can be generated through introduction of an appropriate 17α-substituent.

Significant research efforts have focused on the synthesis and evaluation of compounds designed to either mimic or block the effects of the endogenous androgen, testosterone. While many steroidal compounds can mimic testosterone, relatively few were able to block its effects in target tissues and virtually none were effective in treating hormone responsive prostate cancer (Teutsch, 1995). Nonsteroidal agents, however, such as (hydroxy)flutamide, nilutamide, and bicalutamide (Sciarra, 1990; Tucker, 1988, 1990), have demonstrated clinical efficacy for the treatment of prostatic carcinoma, even though their affinity for the AR is relatively low when compared to testosterone (Kokontis, 1999; Battmann, 1998). Recent publications have disclosed another class of nonsteroidal antiandrogens which have potential as clinically useful agents (Hamann, 1998; Edwards, 1999; Higuchi, 1999; Kong, 2000). Analogs of these compounds also demonstrate agonist/antagonist responses at other nuclear receptors (Pooley, 1998; Zhi, 1998, 1999, 2000). Because the nonsteroidal antiandrogens do not correspond to any current steroid hormone pharmacophore, it is possible that they may primarily effect only the message region (helix-12) of the AR-HBD. A potent interaction at that site would still compete with agonist ligand binding for the address region, not entirely unlike the situation for the dopamine transporter inhibitors where structurally diverse families of ligands not only inhibit dopamine and cocaine binding but also, by associating with overlapping sites, inhibit the binding of each other. Thus, the present invention combines features from both the steroid nucleus (address component) and the nonsteroidal antagonist pharmacophore (message component) (see FIG. 8).

Synthesis and Evaluation of Steroidal Antiandrogens at the 17α-Position of Testoterone Synthesis of the Message Components, Characterization, and Conformational Analysis A combination of organotin chemistry and palladium catalyzed coupling reactions is used for the synthesis of the message components (see FIG. 10). The 1-ethynyl-1-aminoperhydroindanes which would incorporate the C- and D-rings of the steroid nucleus is prepared from the corresponding 1-ethynyl-1-acetoxy analogs using a Cu(I)-assisted aminolysis. The ethynyl cycloalkyl alcohols or amines readily undergo hydrostannation to give the corresponding E- and Z-stannylvinyl intermediates which can be coupled with the requisite mono- or di-substituted aryl iodide under Stille coupling conditions (Farina, 1995; Casado, 1998). Three 3'- or 4'-substituted, three 3'-, 4'-disubstituted, and three 3'-, 5'-disubstituted phenyl iodides are used to generate a total of 18 compounds. While there are no obvious choices for the optimal substituents, the structure activity relationships (SAR) for antiandrogens suggest that electron withdrawing groups (e.g., —$NO_2$, $CF_3$) enhance potency. Therefore, these groups are used with one electron releasing group in the first series (Tucker, 1988). Suzuki coupling reaction is used with vinylboronic acid (Suzuki, 1999). The E-vinylboronic acid is accessed directly by hydroboration of the alkyne with catecholborane followed by hydrolysis. The Z-isomer is obtained from the Z-vinylstannane via iodododestannylation, followed by coupling with bispinacolatodiboron, and hydrolysis.

For the synthesis of the spirocyclic ether or amine message components, the coupling partner for the Z-vinylstannane (or boronic acid) requires an orthoiodo(bromo)phenol derivative. Halogenation of the commercially available 3'- or 4'-substituted phenol gives the intermediate which is initially protected as the silyl ether. The Z-vinyl arene is made by the standard Stille or Suzuki coupling methods. The conditions developed by Buchwald and Hartwig to effect the intramolecular aryl amine/ether formation may be used (Wolfe, 1998, 1999; Yang, 1999; Hartwig, 1998a,b) Deprotection of the phenol, conversion to the triflate, and coupling with an appropriate Pd catalyst, such as $Pd_2(dba)_3$, and an activating ligand, such as BINAP, will effect the cyclization. The final product is provided by the deprotection of the amine.

Each new compound synthesized is characterized by the standard spectrometric methods—high resolution mass spectrometry (HRMS), H-1/C-13-nuclear magnetic resonance spectrometry (NMR) to confirm the proposed molecular structures. Solution conformations is determined by using 1D- and 2D-NMR techniques, methods of which are described above. The use of both conformational analysis and computational methods, more probable solution conformations are identified, which provides information with regard to key structural features and how they influence molecular conformations.

Screening for Androgen Receptor Affinity, Efficacy and Selectivity

Compounds prepared containing the message components may be screened by a bioevaluation protocol already established through a commercially available company (e.g., MDS-Panlabs, located in Bothell, Wash.) to determine their AR affinity, efficacy and selectivity. Receptors from rat ventral prostate tissue may be used to determine the IC50 and Ki values. [H-3] mibolerone may be used as the radioligand. Synthesized hydroxyflutamide, nilutamide, bicalutamide and LG 120907 is evaluated as standard AR ligands. Those new compounds that demonstrate AR affinities >10% that of bicalutamide or LG 120907 will be evaluated for their affinities for the other nuclear receptors. Other sources for receptors and their radioligands include Erα-human recombinant from insect St9 cells, [H-3] estradiol, GR-human Jerkat cells, [H-3] dexamethasone, and PgR-bovine, [H-3] R-5020. Compounds that express a significant selectivity for AR (>10:1) is tested for their efficacy in the rat agonism/antagonism model. In vitro efficacy model for testing the compounds for antagonism is the use of cotransfection and whole cell receptor binding (Hamann, 1998).

Preliminary SARs is determined from the IC50 and Ki data from the screening of the new compounds. E- vs. Z-stereochemistry of the acyclic series of compounds is studied as well as the effects of mono- vs. di-substitution and 3- vs. 4-substitution. The cyclized compounds are compared with the acyclic series- to identify particular substituent trends. The QSAR-CoMFA module of SYBIL is used to clarify the individual parameters (Gantchev, 1994). The physicochemical parameters developed by Hansch may also be used to evaluate the data (Gantchev, 1994). The most potent ligands are analyzed for the lowest energy conformations using QUANTA-CHARMM/mm3 force fields (Wurtz, 1998) and compared with those from the NMR conformational studies to rationalize the initial SAR. This allows for better determination of which substituents are most effective in contributing to AR affinity, selectivity and antihormonal response. Subsequently, the selected substituents is used for incorporation into the address-message composite.

Synthesis of (Nor)Testosterone Derivatives with the Message Component at 17α-Position 17α-ethynyl-(19nor)testoterone and its dihydroderivative (address component) is used as the starting material. The message components may be obtained from commercially available (or readily synthesized) mono- and disubstituted iodophenols. The same message components as with the estrogen study are used—the nilutamide/bicalutamide family of nonsteroidal antagonists and the more potent Ligand Pharmaceutical antagonists. For the message components analogous to flutamide and bicalutamide, the ethylene group is selected as an isosteric substitution for the amide bond (Luthman, 1996). The method for synthesis of the (nor) testosterone derivatives with the message component at the 17α-position is similar to the steps used for the synthesis of antiestrogens described herein. The antiandrogens of the present invention will include the steroid nucleus (A-D rings) and will provide functionality in the A-ring (3 C=O/—OH; 4,5-C=C). As an embodiment, these groups are prepared to protect them as ketals, esters or silyl/enol ethers (Hoyte, 1993; van den Bos, 1998).

REFERENCES

Battmann, T., Branche, C., Borichoux, F., Cerede, E., Philibert, D., Goubet, F., Teutsch, G., Gallard,-Kelly, M. Pharmacological profile of RU58642, a potent systemic antiandrogen for the treatment of androgen-dependent disorders. *J. Steroid Biochem. Molec. Biol.* (1998) 64: 103–111;

Beatson G T, On the treatment of inoperable cases of carcinoma of the mamma: suggestions for a new method of treatment with illustrative cases. *Lancet* ii:104–107 (1896);

Bhatanagar A S, Miller W R. Pharmacology of inhibitors of estrogen biosynthesis. In "Estrogens and Antiestrogens. *Handbook of Experimental Pharmacology*. 136, Vol. II, Oettel M, Schillinger E, Eds., Springer-Verlag, New York (1999), pp. 223–230;

Blatz, P. E.; Estrada, A. *Anal. Chem.* (1972) 44:570–573;

Bowden, K; Heilbron, I. M.; Jones, E. R. H.; Weedon, B. C. L. *J. Chem. Soc.* (1946) 39–45;

Boyd S. On oophorectomy in cancer of the breast. *Br Med J*, ii:1161–1167 (1900);

Brzozowski, A. M., Pike, A. C. W., Dauter, Z., Hubbard, R. E., Bonn, T., Engstrom, O., Ohman, L., Greene, G. L., Gustafsson, J. -A., Carlquist, M. Molecular basis of agonism and antagonism in the estrogen receptor. *Nature* (1997) 389: 753–758;

Carr, F. H.; Price, E. A. *Biochem. J.* (1926) 20:497–501;

Casado, A. L., Espinet, P. Mechanism of the Stille reaction. 1. The transmetalation step. Coupling of RI and R2SnBu3 catalyzed by trans-[PdR1L2](R1 =C6C12F3; R2=vinyl, 4-methoxyphenyl; L=AsPh3). *J. Am. Chem. Soc.* (1998) 120: 8978–8985;

Cole M P, Jones C T A, Todd I D H. A new antiestrogenic agent in late breast cancer. An early appraisal of ICI 46,474. *Br J Cancer* 25:270–275 (1971);

Early Breast Cancer Trialists' Collaborative Group. Tamoxifen for early breast cancer: an overview of the randomized trials. *Lancet* 351:1451–1467 (1998); Edwards, J. P., Higuchi, R. I., Winn, D. T., Pouley, C. L. Fr., Caferro, T. R., Hamann, L. G., Zhi, L., Marschke, K. B., Goldman, M. E., Jones, T. K. Nonsteroidal androgen agonists based on 4-(trifluoromethyl)-2H-pyrano[3,2-g]quinoline. *Bioorg. Med. Chem. Lett.* (1999) 9:1003–1008;

Farina V, Krishnamurthy V, Scott W J. The Stille reaction. *Org Reactions* 50:1–651(1995);

Farrall, M. J.; Frechet J. M. J. *J. Org. Chem.* (1976) 41:3877–3882;

Galbraith, S. M., Duschene, G. M. Androgens and prostate cancer: Biology, pathology and hormonal therapy. *Eur. J. cancer* (1997) 33: 545–554;

Gantchev, T. G., Ali, H., van Lier, J. E. Quantitative structure-activity relationships/comparative molecular field analysis (QSAR/CoMFA)for receptor-binding properties of halogenated estradiol derivatives. *J. Med. Chem.* (1994) 37:4164–4176;

Gordon, A. J.; Ford, R. A. *The Chemists's Companion-A Handbook of Practical Data, Techniques and References*, Wiley: New York, (1972) p 378;

Greenlee, R T et al., (2000) Cancer Statistics 2000, CA, *Cancer J. Clin.*, 50:7–33;

Grese T A, Dodge J A. Selective estrogen receptor modulators (SERMS). *Curr Pharm Design* 4:71–92;

Haas, G. P., Sake W. A. Epidemiology of prostate cancer. *CA-Cancer J. Clin.* (1997) 47:273–287;

Hamann, L. G., Higuchi, R. I., Zhi, L., Edwards, J. P., Wang, X. -N., Marschke, K. B., Kong, J. W., Farmer, L. J., Jones, T. K. Synthesis and biological activity of a novel series of nonsteroidal, peripherally selective androgen receptor antagonists derived from 1,2-dihydrophyridono[5,5-g] quinoline. *J. Med. Chem.* (1998) 41:623–639;

Hartwig, J. F. Transition metal catalyzed synthesis of arylamines and aryl ethers from aryl halides and triflates: Scope and mechanism. *Angew. Chem. Int. Ed.* (1998b) 37:2046–2067;

Hartwig, J. F. Carbon-heteroatom bond-forming reductive eliminations of amines, ethers and sulfides. *Acc. Chem. Res.* (1998a) 31:852–860;

Higuchi, R. I., Edwards, J. P., Caferro, T. R., Ringgenberg, J/D., Kong, J. W., Hamann, L. G., Ariente, K. L., Marschke, K. B., Davis, R. L., Farmer, L. J., Jones, T. K. 4-Alkyl-and 3,4-dialkyl-1,2,3,4-tetrahydro-8-pyridono[5, 6-g]quinolines: Potent nonsteroidal androgen receptor agonists. *Bioorg. Med. Chem. Lett.*(1999) 9:1335–1340;

Hoyte, R. B., Brown, T. J., MacLusky, N. J., Hochberg, R. B. 7a-Methyl-17a-(E-2'-[1–125] iodovinyl)-19-nortestosterone: a new radioligand for the detection of the androgen receptor. *Steroids* (1993) 58:13–23;

Jork, H.; Funk, W.; Fischer,. W.; Wimmer, H. *Thin-Layer Chromatography, Reagent and Detection Method*, VCH: New York, (1990) Vol. 1a;

Klaholz, B. P., Renaud, J. -P., Mitschler, A., Zusi, C., Chambon, P., Gronemeyher, H., Moras, D. Conformational adaptation of agonist to the human nuclear receptor RARγ. *Nature Struct. Biol.* (1998) 5:199–202;

Klinge, C. M. Estrogen receptor interaction with co-activators and co-repressors. *Steroids* (2000) 65:227–251;

Kokontis, J. M., Liao, S. Molecular action of androgen in the normal and neoplastic prostate. *Vitamins and Hormones* (1999) 55:219–307;

Kong, J. W., Hamann, L. G., Ruppar, D. A., Edwards, J. P., Marschke, K. B., Jones, T. K. Effects of isosteric pyridone replacements in androgen receptor antagonists based on 1,2-dihydro-and 1,2,3,4-tetrahydro-2 -2-dimethyl-6-trifluoromethylp8-pyridono[5, 6-g]quinoline. *Bioorg. Med. Chem. Lett.* (2000) 10:411–414;

Landis, S. H., Murray, T., Bolden, S., Wingo, P. A. Cancer statistics-1999.CA-Cancer J. Clin. (1999) 49:8–31;

Levenson A S, Jordan V C. Selective oestrogen receptor modulation: Molecular pharmacology for the millenium. *Eur J Cancer* 35:1628–1639 (1999);

Luthman K. Hacksell, U. Peptides and peptidomimetics. In "A textbook of *Drug Design and Development, 2$^{nd}$ ed.*" Krogsgaard-Larsen, P., Liljefors, T., Madsen, U., eds. Harwood, Amsterdam (1996) pp. 386–406;

McCannon et al., (1993), *Mol. Cell. Endocrinology*, 91:177–183;

McKenna, N. J., Lanz, R. B., O'Malley, B. W. Nuclear receptor coregulators: Cellular and molecular biology. *Endocr. Rev.* (1999) 20:321–344;

Mettlin, C. Recent developments in the epidemiology of prostate cancer. *Eur. J. Cancer* (1997) 33:340–347;

Morales, G. A.; Corbett, J. W.; Degrado, W. F. *J. Org. Chem.* (1998) 63:1172–1177;

Nozaki, K.; Oshima, K.; Utimoto, K. *Tetrahedron* (1989) 45:923–933;

Ornstein, D. K., Dahut, D. L., Liotta, L. A., Emmert-Buck, M. R. Review of AACR meeting: New research approaches in the prevention and cure of prostate cancer, 26 December 1998, Indian Wells, Calif. *Biochem. Biophys. Acta* (1999) 1424: R11-R19;

Pooley, C. L. F., Edwards J. P., Goldman, M. E., Wang, M. -W., Marschke, K. B., Crombie, D. L., Jones, T. K. Discovery and preliminary SAR studies of a novel, non-steroidaql progesterone receptor antagonist pharmacophore. *J. Med. Chem.* (1998) 41:3461–3466;

Renaud, J. P.; Rochel, N.; Ruff, M.; Vivat, V.; Chambon, P.; Gronemeyer, H.; Moras, D. Crystal structure of the RAR-γ ligand binding domain bound to all-trans retinoic acid. *Nature* (1995) 378:681–689;

Resche-Rigon, M., Gronemeyer, H. Therapeutic potential of selective modulators of nuclear receptor action. *Curr. Opin. Chem. Biol.* (1998) 2: 501–507;

Roach, M., III. Current status of androgen suppression and radiotherapy for patients with prostate cancer, *J. Ster. Biochem. Molec. Biol.* (1999) 69:239–245;

Sciarra, F., Toscano, G., Concolino, G., DiSilverio, F. Antiandrogens: Clinical applications.J.Steroid Biochem. Molec. Biol. (1990) 37:349–362;

Scott, J A et al., (1991) *New Molecular Markers of Prognosis in Breast Cancer*, Raven Press, New York, pp. 179–196;

Shiau A K, Barstad D, Loria P M, Cheng L, Kushner P J, Agard D A, Greene G L. The structural basis of estrogen receptor/coactivator recognition and the antagonism of this interaction by tamoxifen. *Cell* 95: 927–937 (1998);

Simons, S. S. Jr. Structure and function of the steroid and nuclear receptor ligand binding domain. In "*Molecular Biology of Steroid and Nuclear Hormone Receptors,*" Freeman, L., ed. Birkhauser, Boston, (1998) pp. 35–104;

Stille, J. K. Pure Appl. Chem. (1985) 57:1771–1780;

Suzuki, A. Recent advances in the cross-coupling reactions of organoboron derivatives with organic electrophiles, 1995–1998. *J. Organomet. Chem.* (1999) 576:147–168;

Tannenbaum, D. M., Wang, Y., Williams, S. P., Sigler, P. B. Crystallographic comparison of the estrogen and progesterone receptor's ligand binding domains. *Proc. Nat. Acad Sci.* (1998) 95: 5998–6003;

Teutsch, G., Nique F., Lemoine, G., Bouchoux, F., Ce're'de, E., Gofflo, D., Philibert, D. General structure-activity correlations of antihormones. *Ann. N.Y. Acad. Sci.* (1995) 761:5–28;

Tsai, M. J., O'Malley, B. W. Molecular mechanisms of action of the steroid/thyroid receptor superfamily mambers. *Ann. Rev. Biochem.* (1994) 63:451–486;

Tucker, H. Nonsteroidal antiandrogens in the treatment of prostate cancer. *Drugs Future* (1990) 15(3):225–265;

Tucker, H., Crook, J. W., Chesterson, G. J., Nonsteroidal anti-androgens. Synthesis and structure-activity relationships of 3-substituted derivatives of 2-hydroxypropionanilides. *J. Med. Chem.* (1988) 31:954–959;

Van Den Bos, J. C., Rijks, L. J. M., van Doremalen, P. A. P. M., de Bruin, K., Janssen, A. G. M., van Royen, E. A. New iodinated progestins as potential ligands for progesterone receptor imaging in breast cancer. Part 1: Synthesis and in vitro pharmacological characterization. *Nucl. Med. Biol.* (1998) 25:781–789;

Weatherman, R. V., Fletterick, R. J., Scanlon, T. S. Nuclear receptor ligands and ligand binding domains. Ann. Rev. Biochem. (1999) 68:559–581;

Williams, S. P., Sigler, P. B. Atomic structure of progesterone complexed with its receptor. *Nature* (1998) 393: 392–396;

Wolfe, J. P., Singh, R. A., Yang, B. H., Buchwald, S. L. Highly reactive palladium catalysts for Suzuki coupling reactions. *J. Amer. Chem. Soc.* (1999) 121: 9550–9561;

Wolfe, J. P., Wagaw, S., Marcoux, J. -F., Buchwald, S. L. Rational development of practical catalysts for aromatic carbon-nitrogen bond formation. *Acc. Chem. Res.* (1998) 31:805–818;

Wurtz, J. -M., Egner, U., Heinrich, N., Moras, Mueller-Fahrnow, A. Three-dimensional models of estrogen receptor ligand binding domain complexes, based on related crystal structures and mutational and structure-activity data. *J. Med. Chem.* (1998) 41:1803–1814;

Yang, B. H., Buchwald, S. L. Palladium-catalyzed amination of aryl halides and sulfonates. *J. Organomet. Chem.* (1999) 576:125–146;

Zhi, L., Tegley, C. M., Pio, B., West, S. J., Marschke, K. B., Mais, D. E., Jones, T. K. Nonsteroidal progesterone antagonists based on the 6-thiophenehydroquinolines. *Bioorg. Med. Chem. Lett.* (2000) 10:415–418;

Zhi, L., Tegley, C. M., Edwards, J. P. West, S. J., Marschke, K. B., Gottardis, M. M., Mais, D. E. Jones, T. K. 5-Alkyl-1,2-dihydrochromeno [3,4-f]quinolines: A novel class of nonsteroidal progesterone receptor modulators. *Bioorg. Med. Chem. Lett.* (1998) 8:3365–3370;

Zhi, L., Tegley, C. M., Marschke, K. B., Mais, D. E., Jones, T. K. 5-Aryl-1,2,3,4-tetrahydrochromeno[3,4-f]quinolin-3-ones as a novel class of progesterone agonist: Effect of A-ring modification. *J. Med. Chem.* (1999) 42: 1466–1472.

EQUIVALENTS

While the present invention has been described in conjunction with a preferred embodiment, one of ordinary skill, after reading the foregoing specification, will be able to effect various changes, substitutions of equivalents, and other alterations to the compositions and approaches set forth herein. It is therefore intended that the protection granted by Letters Patent hereon be limited only by the definitions contained in the appended claims and equivalents thereof.

The invention claimed is:

1. A compound having the structural formula, wherein said compound has a message unit at the 17α-position of an address unit, comprising:

a) an address unit having the structure:

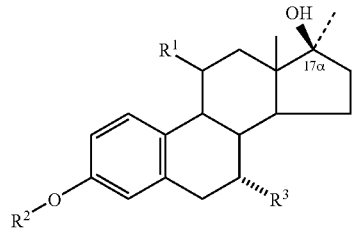

wherein:
$R^1$ is H, $CH_3$, $CH_2CH_3$, OH, $OCH_3$, $OCH_2CH_3$, $C_1$–$C_6$ alkyl, CH=$CH_2$, CH=$CHCH_3$, $CH_2$–aryl;

$R^2$ is H, $CH_3$, $COCH_3$, $CO(CH_2)_nCH_3$, CO–aryl, alkyl, cycloalkyl (ether), ester; and $R^3$ is H, $CH_3$, $CH_2CH_3$, aryl, heteroaryl, $C_1$–$C_6$ alkyl, alkyl ($C_1$–$C_6$) amides, alkyl ($C_1$–$C_6$) sulfide, alkyl ($C_1$–$C_6$) sulfone, alkyl ($C_1$–$C_6$) sulfoxide; and b) a message unit having the structure;

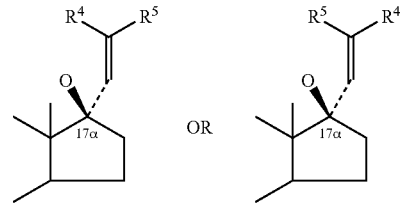

wherein:

$R^4$ is H, $C_1$–$C_4$ alkyl;

$R^5$ is substituted aryl, heteroaryl, fused aryl, —CO-aryl, CO-fused aryl, —CO-heteroaryl, —CO-fused heteroaryl, biaryl, CO-biaryl, ether-linked aryls, ether-linked heteroaryls, amine-linked aryls, amine-linked heteroaryls, aminoalkoxy arene hybrid, or peptidyl hybrid, wherein any substituted aryl, heteroaryl, fused aryl, —CO-aryl, CO-fused aryl, —CO-heteroaryl, —CO-fused heteroaryl, biaryl, CO-biaryl, ether-linked aryls, ether-linked heteroaryls, amine-linked aryls, amine-linked heteroaryls, aminoalkoxy arene hybrid and peptidyl hybrid, may optionally be substituted, independently, with H, $CH_3$, OH, $OCH_3$, $OCF_3$, $N(CH_3)_2$, $NHCOCH_3$, aryl, $CO_2CH_3$, $CONH_2$, $C_1$–$C_4$ alkyl, $(CF_2)_nF$ wherein n=1–4, Cl, Br, I, F, $O(CH_2)_nH$ wherein n=1–4, $NO_2$, $NH_2$, $NHCOR^4$, $CO_2H$, $CO_2R^4$, $CONHR^4$, amyl, thioether, $SR^6$, $S(O)R^6$, $SO_2NR^6R^7$; wherein $R^4$ has the definition given above; wherein $R^6$ is H, $C_1$–$C_4$ alkyl or perfluoroalkyl, aryl, heteroaryl, optionally substituted allyl, arylmethyl, alkynyl, or alkenyl; wherein $R^7$ is H, $C_1$–$C_4$ alkyl or perfluoroalkyl, aryl, heteroaryl, optionally substituted allyl, arylmethyl, $OR^8$ or $NHR^8$; wherein $R^8$ is H, $C_1$–$C_6$ alkyl or perfluoroalkyl, aryl, heteroaryl, optionally substituted allyl, arylmethyl, $SO_2R^6$ or $S(O)R^6$, wherein $R^6$ has the definition given above; and wherein $R^5$ can be in either the E or Z configuration in relation to the 17α-position of said address unit.

2. A compound having the structural formula, wherein said compound has a message unit at the 17α-position of an address unit, comprising:

a) an address unit having one of the following different structures;

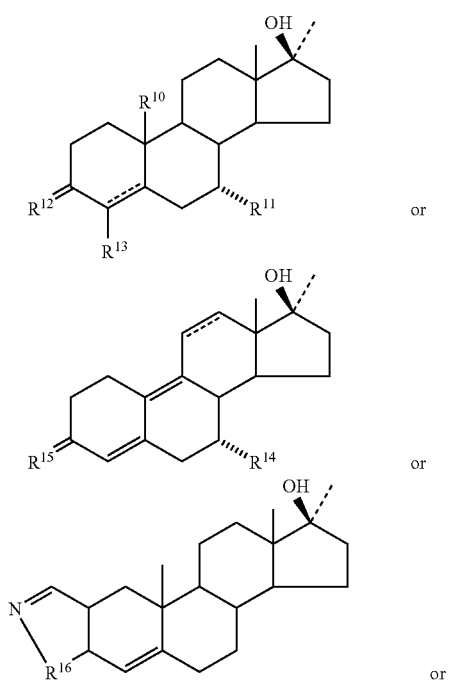

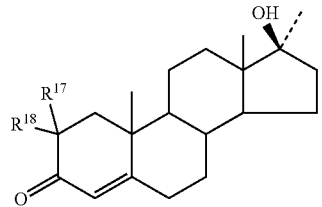

wherein $R^{10}$ is H, $CH_3$;

$R^{11}$ is H, $C_1$–$C_4$ alkyl;

$R^{12}$ is O, (H, OH);

$R^{13}$ is H, OH, Cl, Br, I, $CH_3$;

$R^{14}$ is H, $C_1$–$C_4$ alkyl;

$R^{15}$ is O, (H, OH);

$R^{16}$ is O, NH; and $R^{17}$ through $R^{18}$ each independently is H, $CH_3$; and b) a message unit having the structure;

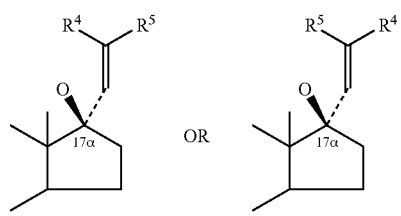

wherein;

$R^4$ is H, $C_1$–$C_4$ alkyl:

$R^5$ is aryl, heteroaryl, fused aryl, —CO-aryl, CO-fused aryl, —CO-heteroaryl, —CO-fused heteroaryl, biaryl, CO-biaryl, ether-linked aryls, ether-linked heteroaryls, amine-linked aryls, or amine-linked heteroaryls, wherein any aryl, heteroaryl, fused aryl, —CO-aryl, CO-fused aryl, —CO-heteroaryl, —CO-fused heteroaryl, biaryl, CO-biaryl, ether-linked aryls, ether-linked heteroaryls, amine-linked aryls, and amine-linked heteroaryls may optionally be substituted, independently, with H, $CH_3$, OH, $OCH_3$, $OCF_3$, $N(CH_3)_2$, $NHCOCH_3$, aryl, $CO_2CH_3$, $CONH_2$, $C_1$–$C_4$ alkyl, $(CF_2)_nF$ wherein n=1–4, Cl, Br, I, F, $O(CH_2)_nH$ wherein n=1–4, $NO_2$, $NH_2$, $NHCOR^4$, $CO_2H$, $CO_2R^4$, $CONHR^4$, amyl, thioether, $SR^6$, $S(O)R^6$, $SO_2R^6$, $SO_2NR^6R^7$; wherein $R^4$ has the definition given above; wherein $R^6$ is H, $C_1$–$C_4$ alkyl or perfluoroalkyl, aryl, heteroaryl, optionally substituted allyl, arylmethyl, alkynyl, or alkynyl; wherein $R^7$ is H, $C_1$–$C_4$ alkyl or perfluoroalkyl, aryl, heteroaryl, optionally substituted allyl, arylmethyl, $OR^8$ or $NHR^8$; wherein $R^8$ is H, $C_1$–$C_6$ alkyl or perfluoroalkyl, aryl, heteroaryl, optionally substituted allyl, arylmethyl, $SO_2R^6$ or $S(O)R^6$, wherein $R^6$ has the definition given above ; and wherein $R^5$ can be in either the E or Z configuration in relation to the 17α-position of the address unit.

* * * * *

UNITED STATES PATENT AND TRADEMARK OFFICE
CERTIFICATE OF CORRECTION

| | |
|---|---|
| PATENT NO. | : 7,041,839 B2 |
| APPLICATION NO. | : 10/297310 |
| DATED | : May 9, 2006 |
| INVENTOR(S) | : Robert N. Hanson et al. |

It is certified that error appears in the above-identified patent and that said Letters Patent is hereby corrected as shown below:

Title page, (75) Inventors "Newtown" should read --Newton--;

Column 3, line 62, "$NHCOR_1$" should read --$NHCOR^4$--;

Column 3, line 63, "$CONHR4$" should read --$CONHR^4$--;

Column 11, line 19, "above." should read --the indicated positions with substituents as described above.--;

Column 16, line 44, "$CDCl_3$" should read --CDC13--;

Column 18, line 48, "6)" should read --$\delta$--;

Column 18, line 49, "17P" should read --$17\beta$--;

Column 18, line 55, "8)" should read --$\delta$--;

Column 19, line 1, "6)" should read --$\delta$--;

Column 19, line 30, "6)" should read --$\delta$---;

Column 19, line 31, "($Cl_2$)" should read --($C_{12}$)--;

Column 19, line 32, "($Cl_4$) should read --($C_{14}$)--;

Column 19, line 40, "$17\alpha$-diol" should read --$17\beta$-diol--;

Column 19, line 42, "6)" should read --$\delta$)--;

Column 19, line 44, "17P hydroxyl-H)" should read --$17\beta$ hydroxyl-H)--;

Column 19, line 62, "(Cg)" should read --($C_9$)--;

Column 20, line 4, "6)" should read --$\delta$)--;

Column 20, line 11, "6)" should read --$\delta$)--;

Column 20, line 13, "(Cg)" should read --($C_9$)--;

UNITED STATES PATENT AND TRADEMARK OFFICE
CERTIFICATE OF CORRECTION

PATENT NO.       : 7,041,839 B2
APPLICATION NO.  : 10/297310
DATED            : May 9, 2006
INVENTOR(S)      : Robert N. Hanson et al.

It is certified that error appears in the above-identified patent and that said Letters Patent is hereby corrected as shown below:

Column 20, line 14,   "(C1)" should read --($C_1$)--;

Column 20, line 24,   "17P" should read --17β--;

Column 20, line 30,   "6)" should read --δ--;

Column 20, line 32,   "($C1_2$)" should read --($C_{12}$)--;

Column 20, line 32,   "(Cg)" should read --($C_9$)--;

Column 20, line 34,   "(C25)" should read --($C_{25}$)--;

Column 20, line 42,   "17P hydroxyl-H)" should read --17β hydroxyl-H)--;

Column 20, line 45,   "C1-H)" should read --$C_1$-H)--;

Column 20, line 49,   "(Cg)" should read --($C_9$)--;

Column 20, line 51,   "(C10)" should read --($C_{10}$)--;

Column 21, line 36,   "The loading[1]" indicates there should be a footnote listed at the bottom of the page. Please insert the following footnote:
--[1]The loading capacities for the functionalized resins were expressed in mmol $g^{-1}$ and for the following steps were expressed in % or mmol $g^{-1}$.--;

Column 21, line 40,   "g-1 of Z)" should read --$g^{-1}$ of Z)--;

Column 30, claim 1, lines 35-45, the structure should read as follows:

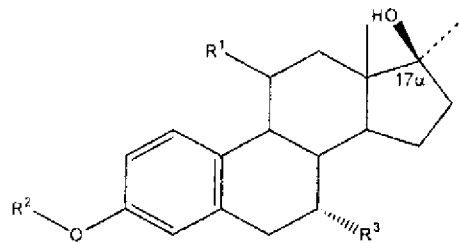

UNITED STATES PATENT AND TRADEMARK OFFICE
CERTIFICATE OF CORRECTION

PATENT NO.        : 7,041,839 B2                                   Page 3 of 5
APPLICATION NO.   : 10/297310
DATED             : May 9, 2006
INVENTOR(S)       : Robert N. Hanson et al.

It is certified that error appears in the above-identified patent and that said Letters Patent is hereby corrected as shown below:

Column 30, claim 1, lines 56-66, the structures should read as follows:

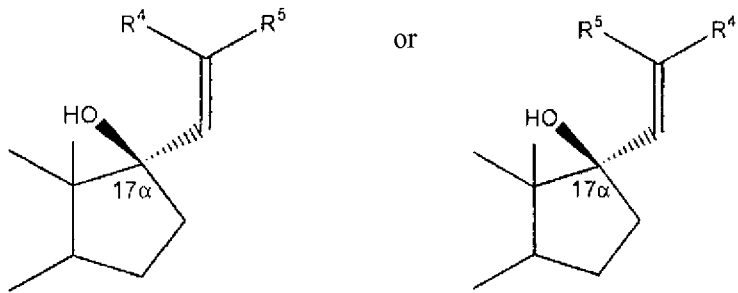

Column 31, claim 2, lines 35-62, the structures should read as follows:

or
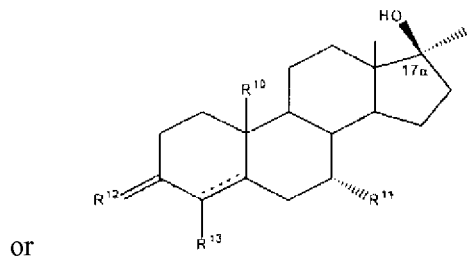

or
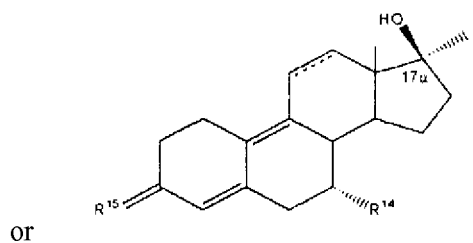

or
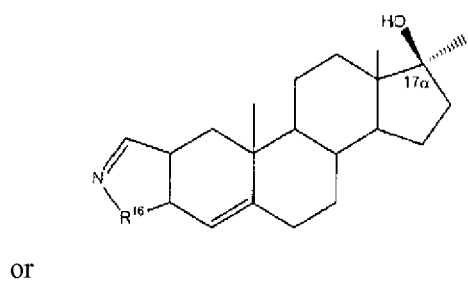

UNITED STATES PATENT AND TRADEMARK OFFICE
CERTIFICATE OF CORRECTION

PATENT NO.         : 7,041,839 B2
APPLICATION NO.    : 10/297310
DATED              : May 9, 2006
INVENTOR(S)        : Robert N. Hanson et al.

It is certified that error appears in the above-identified patent and that said Letters Patent is hereby corrected as shown below:

Column 32, claim 2, lines 1-10, the continued structure should read as follows;

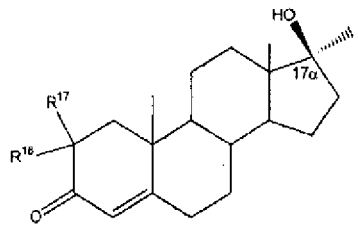

Column 32, claim 2, lines 23-33, the structures should read as follows:

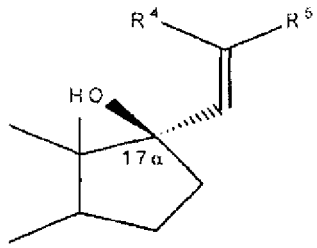

or

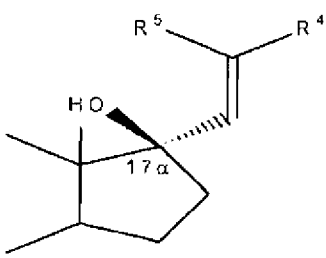

UNITED STATES PATENT AND TRADEMARK OFFICE
CERTIFICATE OF CORRECTION

PATENT NO. : 7,041,839 B2
APPLICATION NO. : 10/297310
DATED : May 9, 2006
INVENTOR(S) : Robert N. Hanson et al.

It is certified that error appears in the above-identified patent and that said Letters Patent is hereby corrected as shown below:

Column 32, claim 2, line 39, "heteroayis" should read --heteroaryls--; and

Column 32, claim 2, line 53, "alkynyl, or alkynyl;" should read --alkynyl, or alkenyl;--.

Signed and Sealed this

Second Day of June, 2009

JOHN DOLL
*Acting Director of the United States Patent and Trademark Office*